(12) United States Patent
Joo et al.

(10) Patent No.: US 6,171,256 B1
(45) Date of Patent: Jan. 9, 2001

(54) METHOD AND APPARATUS FOR DETECTING A CONDITION ASSOCIATED WITH ACUTE CARDIAC ISCHEMIA

(75) Inventors: Tae H. Joo, Redmond; David R. Hampton; Paul W. Schmitt, both of Woodinville; Douglas K. Medema, Everett; Robert A. Niskanen, Seattle, all of WA (US)

(73) Assignee: Physio-Control Manufacturing Corporation, Redmond, WA (US)

( * ) Notice: Under 35 U.S.C. 154(b), the term of this patent shall be extended for 0 days.

(21) Appl. No.: 09/209,879

(22) Filed: Dec. 11, 1998

Related U.S. Application Data

(60) Provisional application No. 60/083,722, filed on Apr. 30, 1998, and provisional application No. 60/100,391, filed on Sep. 15, 1998.

(51) Int. Cl.[7] ............................................. A61B 5/0402
(52) U.S. Cl. ................................................... 600/508
(58) Field of Search ................................... 600/508, 509, 600/512, 515, 516

(56) References Cited

U.S. PATENT DOCUMENTS

| | | | |
|---|---|---|---|
| 5,020,540 | * | 6/1991 | Chamoun .............................. 600/509 |
| 5,634,469 | | 6/1997 | Bruder et al. . | |

FOREIGN PATENT DOCUMENTS

| | | |
|---|---|---|
| 0 512 719 A2 | 11/1992 | (EP) . |
| 0 735 500 A2 | 10/1996 | (EP) . |
| WO 98/40010 | 9/1998 | (WO) . |

\* cited by examiner

Primary Examiner—George R. Evanisko
(74) Attorney, Agent, or Firm—Christensen O'Connor; Johnson Kindness PLLC

(57) ABSTRACT

A device (10) that detects and reports the presence of an acute cardiac ischemic condition in a patient includes sensing electrodes (12, 14, 16, 18, 20, 22, 24, 26, 28, and 30) placed on a patient for acquiring multiple (e.g., twelve) lead ECG data from the patient. The device evaluates the acquired ECG data by analyzing global features derived from the ECG data. Global features include projection coefficients calculated from projecting a concatenated vector of representative heartbeat data onto sets of basis vectors that define an acute cardiac ischemic ECG subspace and a non-ischemic ECG subspace. A classifier evaluates the global features to determine whether an acute cardiac ischemic condition is detected. In a further embodiment of the invention, one or more classifiers evaluate local features, such as local morphological features and patient clinical information, in addition to the global features to determine whether an acute cardiac ischemic condition is detected. The device (10) may be configured with an adjustable sensitivity/specificity operating point. The result of the evaluation is reported to the user of the device.

55 Claims, 16 Drawing Sheets

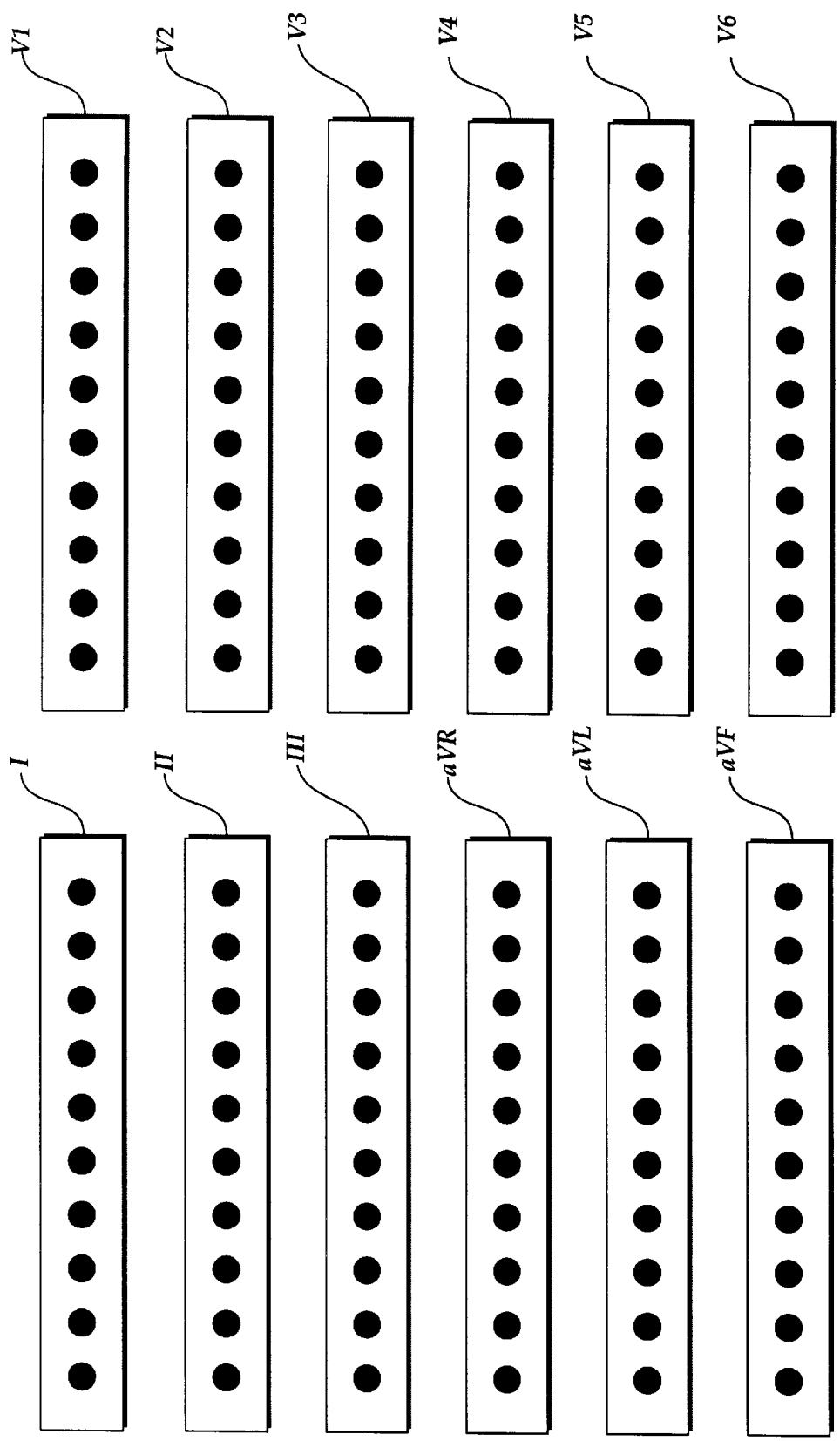
Fig.9. REPRESENTATIVE HEARTBEAT DATA

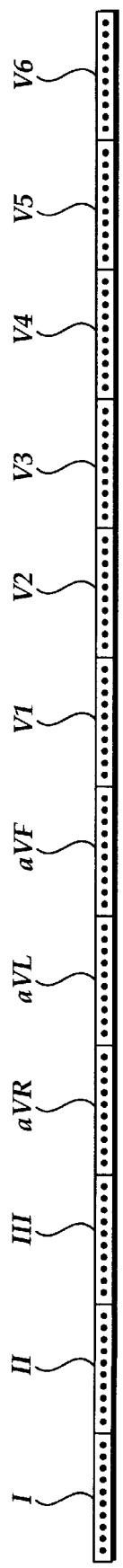
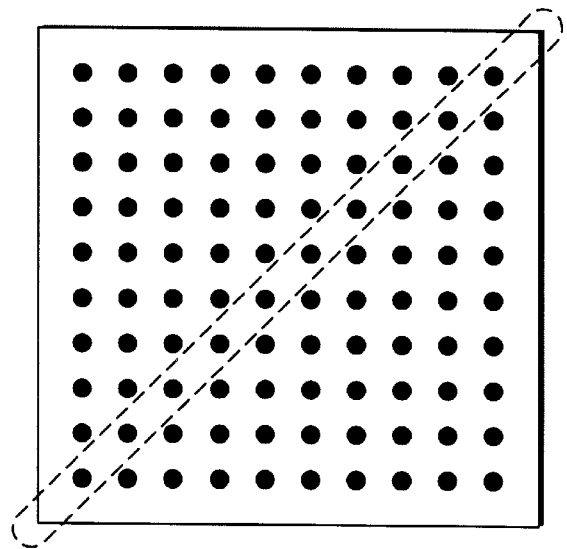
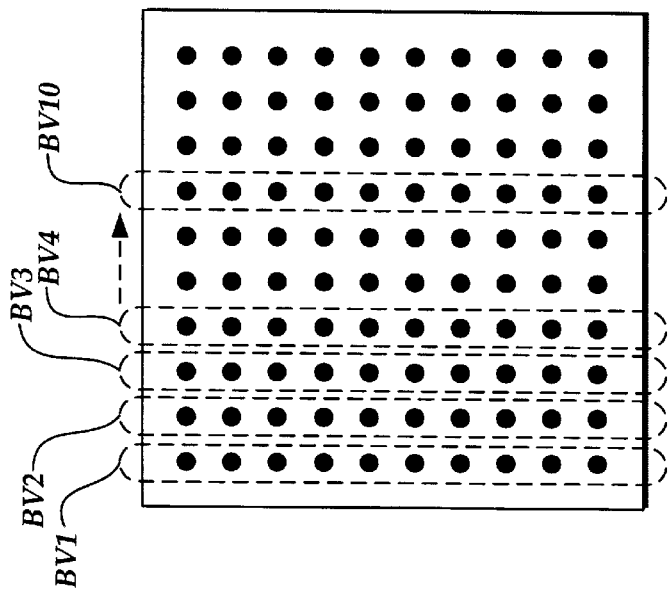
*Fig.10.* REPRESENTATIVE HEARTBEAT VECTOR X
*Fig.11A.* MATRIX V
*Fig.11B.* MATRIX Λ

*GLOBAL FEATURE VECTOR f*

METHOD AND APPARATUS FOR DETECTING A CONDITION ASSOCIATED WITH ACUTE CARDIAC ISCHEMIA

RELATED APPLICATIONS

This application claims the benefit of U.S. Provisional Application Serial No. 60/083,722 filed Apr. 30, 1998, and U.S. Provisional Application Serial No. 60/100,391 filed Sep. 15, 1998.

FIELD OF THE INVENTION

The present invention relates generally to the analysis of cardiac electrical activity, and more specifically, to the evaluation of electrocardiogram data to detect and report cardiac abnormalities.

BACKGROUND OF THE INVENTION

A variety of physiological processes are electrically mediated and produce associated electrical signals. For example, the sinoatrial node in a human heart generates an electrical pulse that triggers the remainder of a heartbeat in a normally functioning heart. This pulse propagates through the heart's normal conduction pathways producing electrical signals that can be observed on the surface of a patient's body. Monitoring and analysis of such electrical signals have proved beneficial in evaluating the function of a patient's heart, including the detection of conditions associated with acute cardiac ischemia.

Monitoring of a patient's cardiac electrical activity is conventionally performed using a 12-lead electrocardiogram (ECG) system that includes a monitor and ten electrodes attached to a patient. A conventional 12-lead ECG system monitors the voltages sensed by the ten electrodes and generates twelve combinations of these voltages to produce the "leads" required by the 12-lead ECG system. Of the ten electrodes in a 12-lead ECG system, four are "limb" electrodes typically placed on or near each of a patient's four limbs, and six are "precordial" electrodes positioned on the patient's chest over the heart. As an electrical impulse propagates through the heart, the monitor repetitively measures the voltages sensed by the electrodes. Although the electrodes collectively monitor the same heartbeats, the electrodes sense different voltages due to their placement with respect to the patient's heart. A time sequence of monitored voltages is used to produce ECG lead data. An ECG monitor typically plots this data to provide graphical waveforms representing the heart's electrical activity for each lead being monitored.

An example of an ECG waveform is shown in FIG. 1. For purposes of analysis, an ECG waveform produced over a time interval corresponding to one cardiac cycle or "heartbeat" is divided into a number of waves. The portion of a waveform representing depolarization of the atrial muscle fibers is referred to as the "P" wave. Depolarization of the ventricular muscle fibers is collectively represented by the "Q," "R," and "S" waves of the waveform. The portion of the waveform representing repolarization of the ventricular muscle fibers is known as the "T" wave. Between heartbeats, an ECG waveform returns to an "isopotential" line. FIG. 1 also illustrates selected fiducial points labeled "q", "j", "t1", and "t2". Fiducial points define the boundaries of selected features and are used in measuring characteristics of an ECG waveform, such as the start and end of a heartbeat and the elevation of the ST portion of a heartbeat. The "q" point shown in FIG. 1 represents the start of the Q wave, the "j" point represents the end of the QRS complex, the "t1" point represents the start of the T wave, and the "t2" point represents the end of the T wave.

As noted, an analysis of a patient's ECG may assist in detecting acute cardiac ischemia in the patient. As a matter of background, acute cardiac ischemia is a condition that arises from chronic or sudden onset of deprivation of blood, and hence oxygen, to muscles of the heart. If an ischemic condition is severe or prolonged, it can result in irreversible death or damage to myocardial cells (i.e., an infarction). A chronic cardiac ischemic condition, angina, is typically caused by narrowing of the coronary arteries due to spasms of the wall muscles or partial blockage by plaques. A sudden cardiac ischemic condition may be caused by a clot blocking the passage of blood in the coronary arteries. Symptoms of a cardiac ischemic event may include chest pain and pain radiating through the extremities, but not all such events present these symptoms. Current medical intervention for severe acute ischemic events includes the administration of a class of drugs called thrombolytics that dissolve clots in the occluded coronary artery, and emergent PTCA, a medical procedure that opens the artery by inflating a balloon inside the clot to make a passage for circulation.

The amount of damage done to a heart by an ischemic event depends, in part, on the amount of time that lapses before treatment is provided. Therefore, ECG data should be evaluated as early as possible so that functional changes associated with cardiac ischemia can be detected and reported as early as possible. With early detection of acute cardiac ischemia, appropriate treatment can take place as early as possible and, thereby, maximize the preservation of myocardium. The American Heart Association recommends that a patient with suspected acute cardiac ischemia be evaluated by a physician using a 12-lead ECG within ten minutes of arrival at a hospital emergency department. Unfortunately, outside of a hospital, highly trained medical personnel are not always available to meet a patient's immediate needs. Quite often, a first responding caregiver to a patient in the field may not be competent in evaluating ECG waveforms to detect acute cardiac ischemic events. A need, therefore, exists for a device that not only obtains ECG data, but also quickly evaluates and automatically produces a preliminary diagnosis that an acute cardiac ischemic condition has been detected.

Traditionally, acute cardiac ischemic conditions are detected by a physician's visual evaluation of 12-lead ECG waveforms. A physician typically selects one or more leads in the 12-lead ECG and makes an initial assessment by comparing selected features of the patient's ECG waveforms to equivalent features of other persons' ECG waveforms that are representative of various abnormal conditions. A physician may also look at the patient's ECG waveforms over time and evaluate any changes in waveform shape. A number of waveform features have been identified as useful in diagnosing acute cardiac ischemic conditions. Customarily, a physician observes the extent to which the ST portion of a waveform exceeds the isopotential line (i.e., the ST elevation) and uses this information to determine if an acute ischemic event has occurred. Nevertheless, because of the subtleties involved in evaluating ECG waveforms, even highly trained individuals often fail to correctly diagnose an acute cardiac ischemic event when evaluating an ECG using traditional features alone. More subtle, globally distributed ECG features remain undetected. A deed, therefore, exists for more accurate ways of detecting and reporting acute cardiac ischemic events.

In recent years, there have been efforts to develop enhanced ECG waveform interpretation based on computer analysis. Conventional computer processes used for ECG waveform analysis are based on heuristics derived from the experience of expert physicians. Such processes implement rules that attempt to simulate an expert physician's reasoning but perform no better than the expert. In practice, many such processes perform more poorly than human expert evaluation.

Furthermore, when a conventional heuristic process is used, it is difficult to choose an optimal operating point for the device in terms of sensitivity (i.e., detecting true positives) and specificity (i.e., avoiding false positives). A device tuned to be more sensitive is typically less specific, while a device tuned to be more specific is typically less sensitive. A typical sensitivity/specificity tradeoff is illustrated by a receiver operating characteristics (ROC) curve, an example of which is shown in FIG. 15. Using a conventional heuristic process, it is difficult to make the sensitivity/specificity tradeoff explicit; thus, the selection of an operating point on the ROC curve is often made in a suboptimal, ad hoc manner. As such, there is a need for an apparatus and method that can provide better performance in terms of sensitivity and specificity and further provide for selecting a sensitivity/specificity tradeoff in a more systematic way.

The present invention provides a method and apparatus having such features, as well as addressing other shortcomings in the prior art.

SUMMARY OF THE INVENTION

In accordance with the present invention, globally-distributed features in a patient's ECG are extracted and analyzed to detect an acute cardiac ischemic condition. First, representative heartbeat data for a patient is calculated from the patient's raw ECG data for each of the leads obtained. The representative heartbeat data from each lead is concatenated to form a vector of representative heartbeat data for the set of measured leads. The concatenated vector of representative heartbeat data is then mathematically projected onto predetermined basis vectors that define signal subspaces of ECGs exhibiting acute cardiac ischemic and non-ischemic conditions. The resulting projection coefficients are "global features" that are evaluated by a classifier to determine whether the global features are indicative of an acute cardiac ischemic condition. Analysis of global features according to the present invention has been found to improve sensitivity while maintaining high specificity as compared to an analysis performed by conventional ECG analysis.

In accordance with further aspects of the invention, local features may be analyzed in addition to global features to further enhance diagnostic accuracy. Local features include measures of morphological features defined for a local time interval less than the duration of a representative heartbeat. An example of a local morphological feature is a measure of ST elevation derived from individual lead data. Clinical information, such as a patient's age and sex, may also be included in the analysis as local features. The local features and global features are either separately evaluated with the results combined, or evaluated in combination to produce a single result, yielding a final decision of whether an acute cardiac ischemic condition is present in the patient.

In accordance with other aspects of this invention, a device incorporating the present invention preferably has an adjustable sensitivity/specificity operating point. The sensitivity/specificity operating point is selected by adjusting the threshold in the classifier that determines the probability of detection of an acute cardiac ischemic condition.

The sensitivity/specificity operating point may be set by the manufacturer of the device, by the purchaser of the device, or by a user of the device. For example, if the sensitivity/specificity operating point of the device is set for a high level of sensitivity for detection of an acute cardiac ischemic event, the device functions as a screening tool that identifies candidates at risk. In a setting where a decision to treat a patient is being made, the operating point of the device can be readjusted for a high level of specificity to confirm the diagnosis of acute cardiac ischemia in the patient.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 9 is a pictorial diagram of twelve leads of representative heartbeat data generated by the acute cardiac ischemia detection process shown in FIG. 4;

FIG. 10 is a pictorial diagram of a concatenated representative heartbeat vector $\underline{x}$ that includes the representative heartbeat data depicted in FIG. 9 and generated by the acute cardiac ischemia detection process shown in FIG. 4;

FIGS. 11A and 11B are pictorial diagrams of matrices V and Λ produced during the basis vector derivation process shown in FIG. 7 by performing a Karhunen-Loeve transformation on a correlation matrix R calculated from ECG data obtained from a training population of patients;

DETAILED DESCRIPTION OF THE PREFERRED EMBODIMENT

Figure 2:
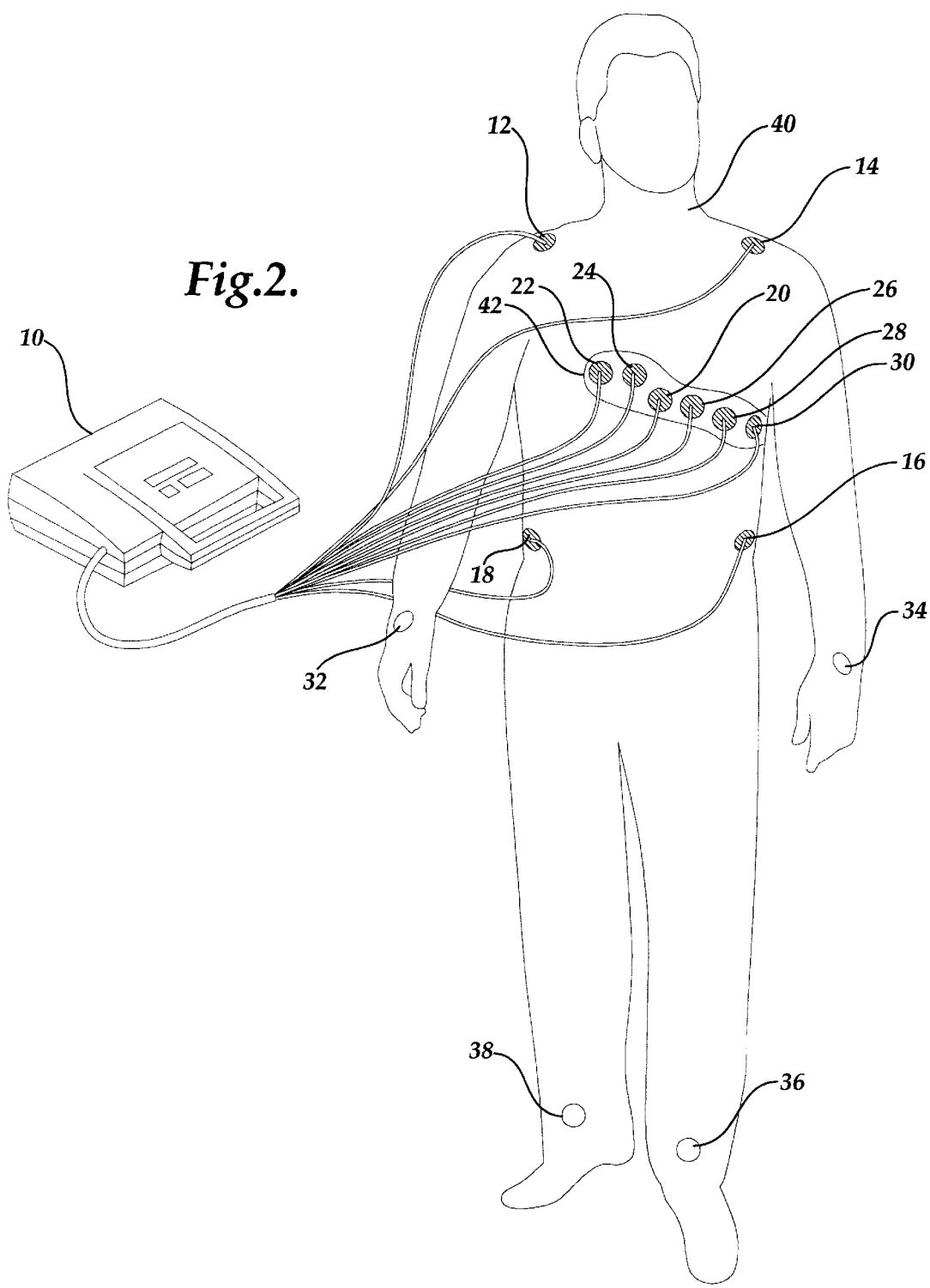
FIG. 2 depicts a device configured to operate in accordance with the present invention, with ten electrodes attached to a patient.

In regard to the present invention, acute cardiac ischemia includes conditions, both chronic and sudden, that result in a deprivation of blood, and hence oxygen, to the muscles of the heart, thus requiring urgent treatment if the long-term viability of the cardiac muscle cells is to be maintained. While these conditions are reversible at the time of detection, these conditions will result in permanent damage to the cardiac muscle cells if sufficient blood flow is not restored. FIG. 2 depicts a device 10 that detects and reports cardiac abnormalities associated with acute cardiac ischemia in accordance with the present invention. When the device 10 is attached to a patient via a plurality of sensing electrodes (e.g., ten electrodes), the device 10 obtains ECG data from the patient, automatically evaluates the data, and reports whether the data indicates an acute cardiac ischemic condition in the patient.

The ten electrodes shown in FIG. 2 are attached to the skin of the patient 40 at a variety of locations. First and second sensing electrodes 12 and 14 are shown attached to the right and left shoulder areas of the patient 40, respectively. Third and fourth sensing electrodes 16 and 18 are shown attached to the left and right side areas of the patient's torso, respectively, near the patient's legs. A fifth sensing electrode 20 is shown attached to the patient's chest area over the heart. Sixth through tenth sensing electrodes 22, 24, 26, 28, and 30 are also spread across the chest of the patient 40.

The ten electrodes shown in FIG. 2 are placed in the standard positions for a 12-lead ECG. The first through fourth sensing electrodes 12, 14, 16, and 18 are known as "limb" electrodes. The fifth through tenth sensing electrodes 20, 22, 24, 26, 28, and 30 are known as "precordial" electrodes. The signals received from the ten electrodes are used to produce 12-lead ECG data in a manner well-known to those skilled in ECG technology. Since the techniques for producing 12-lead ECG data from ten sensing electrodes is well-known and does not form part of this invention, how 12-lead ECG data is produced is not described here. As is conventional, the twelve leads are identified as the I, II, III, aVR, aVL, aVF, V1, V2, V3, V4, V5, and V6 leads.

For a user's convenience, the precordial electrodes may be embodied in a single patch 42. The patch 42 is designed for quick and easy placement of the precordial electrodes on the patient's chest and may be used to reduce the amount of cabling needed to connect the precordial electrodes to the device 10. In the event a patch 42 is not used, each of the precordial electrodes may be individually attached to the patient 40.

Although FIG. 2 shows electrode placement in accordance with one actual embodiment of the invention, it will be appreciated that the electrodes may be placed at alternative locations. For example, the sensing electrodes 12, 14, 16, and 18 may be placed at the ends of the limbs of the patient 40 as indicated by the open circles 32, 34, 36, and 38, respectively. Moreover, it will be appreciated from the discussion below that a device formed according to the present invention may use an alternative number of electrodes other than ten sensing electrodes (i.e., more or less sensing electrodes than shown in FIG. 2). Regardless of the number of sensing electrodes chosen, one or more leads of ECG data are derived from the signals sensed by the electrodes. These leads, which may be a subset selected from a larger set of leads potentially derived from the ECG signals sensed by the electrodes, are referred to herein as the "available leads."

Figure 3:
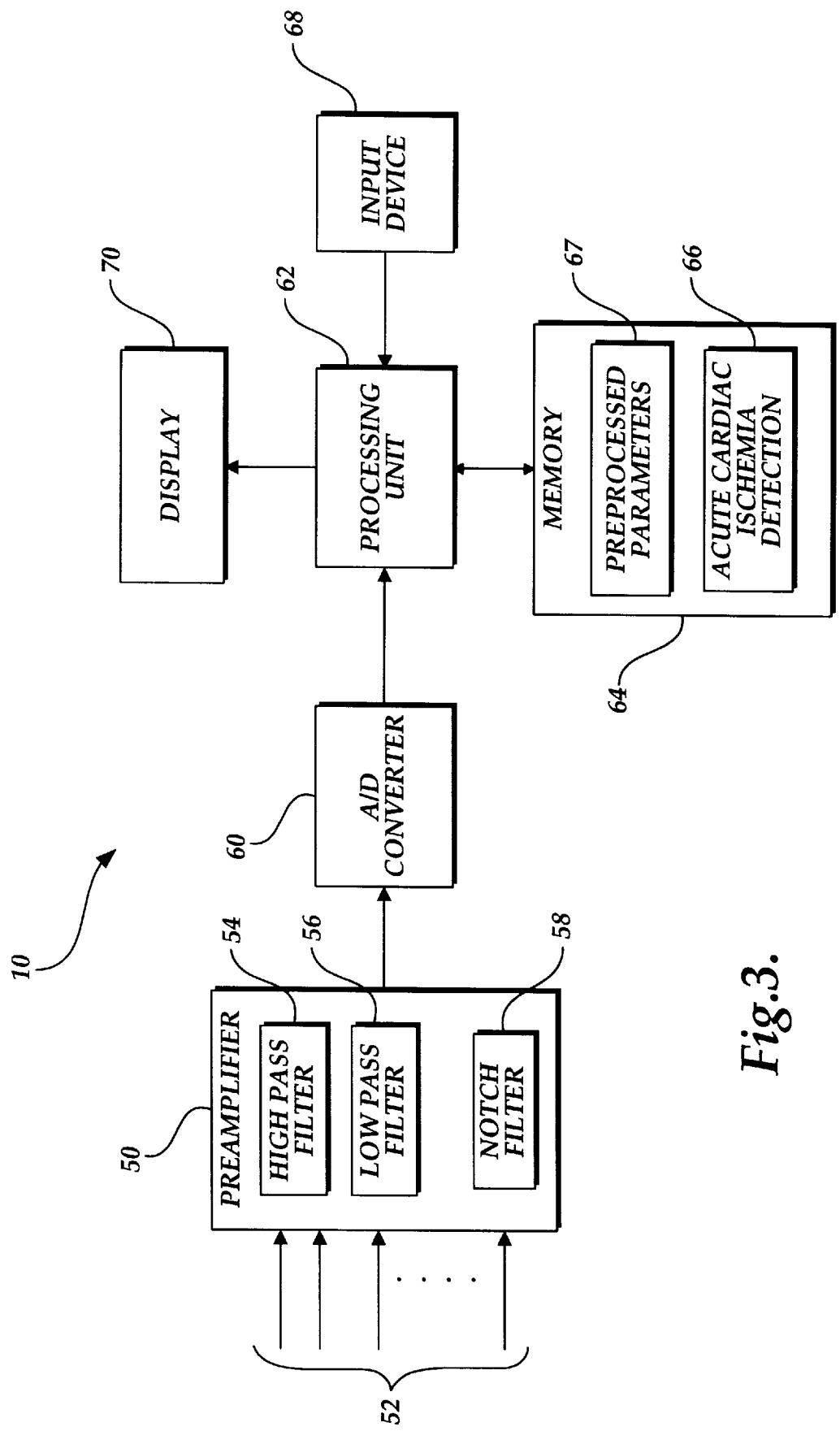
FIG. 3 is a block diagram of the major components of the device shown in FIG. 2.

FIG. 3 is a block diagram illustrating the major components of the device 10 shown in FIG. 2. ECG signals sensed by the sensing electrodes described above (not shown in FIG. 3) are communicated to a preamplifier 50 via lines 52. The preamplifier 50 both amplifies and filters the ECG signals. Amplification is required because the strength of the signals sensed by the electrodes is generally too low (i.e., in millivolts) to be analyzed by the circuitry of the device. The preamplifier 50 may amplify the ECG signals on lines 52 by a factor of 1,000 or more.

The amplified ECG signals are filtered to eliminate noise and other signal contaminants. In one actual embodiment of the invention, the filtering includes a high-pass filter 54 that attenuates low frequency signals (e.g., frequencies below 0.05 Hertz), a low-pass filter 56 that attenuates high frequency signals (e.g., frequencies above 150 Hertz), and a notch filter 58 configured to attenuate signals at a particular frequency (e.g., 50 or 60 Hertz, depending on the local line power frequency). Alternative embodiments of the present invention may include further signal filtering to adapt the device for use in a particular environment.

The amplified and filtered ECG signals are converted into digital ECG data by an analog-to-digital (A/D) converter 60. In the embodiment shown in FIG. 3, the ECG signals are multiplexed by the preamplifier 50 and serially communicated to the A/D converter 60. Alternatively, the ECG signals may be communicated in parallel from the preamplifier 50 to the A/D converter 60 via separate lines for each of the signals (not shown) and multiplexed by the A/D converter. Still further, a separate A/D converter can be provided for each amplified and filtered ECG signal and the output of the multiple A/D converters multiplexed.

The digital ECG data produced by the A/D converter(s) is applied to a processing unit 62 for further processing and evaluation. A memory 64 in communication with the processing unit 62 stores the digital ECG data and other data subsequently generated by the acute cardiac ischemia detection process described in more detail below. The memory 64 also stores an acute cardiac ischemia detection process 66 in the form of computer program instructions that, when executed by the processing unit 62, evaluates the digital ECG data and detects the occurrence of acute cardiac ischemia. The memory 64 also stores preprocessed parameters 67 derived earlier from patients in a training population during a training phase (described below). The preprocessed parameters 67 are used by the acute cardiac ischemia detection process 66 to evaluate the ECG of a current patient for acute cardiac ischemia.

Although analog signal filters 54, 56, and 58 are shown in FIG. 3 and described above, those skilled in the art will appreciate that, alternatively, digital filtering after the ECG signals are converted from analog form to digital form can be used, if desired. Furthermore, filtering of the ECG data can be performed after the data is stored in the memory 64, rather than being performed before storage, as shown.

FIG. 3 also depicts an input device 68 and a display 70 in communication with the processing unit 62 for exchanging information with a user of the device. The input device 68 allows a user to input information and selectively adjust the operation of the device while the display 70 allows the device to report the results of an ECG evaluation to the user. The display 70 also permits the device to communicate instructions to the user.

Those of ordinary skill in the art will appreciate that various devices may be used to implement the function of the components shown in FIG. 3. For example, the processing unit 62 may be a microprocessor controlled by computer program instructions stored in the memory 64. The memory 64 may include nonvolatile memory in the form of read-only memory (e.g., EPROMs), storage memory (e.g., a hard drive), and volatile memory in the form of a random access memory (RAM). The input device 68 may include keys, dials, or switches. Similarly, the display 70 may be a combination of lights or a text display screen, e.g., AMLCD, LCD, or printer. Audible alerts may also be provided. The construction of suitable signal amplifiers, filters, and analog-to-digital converters are well-known to those with ordinary skill in the art and in many cases are readily available in off-the-shelf devices.

As part of an analog-to-digital conversion process, ECG signals sensed by the electrodes are sampled to obtain discrete voltage values at discrete time intervals. The rate at which the ECG signals are sampled depends on the configuration of the analog-to-digital converter 60. In one actual embodiment of the present invention, ECG signals are sampled at a rate of 500 samples per second. Those of ordinary skill in the art will appreciate that other sampling rates may be used.

As will be more readily understood from the discussion below, the device 10 not only acquires ECG data but also evaluates the data and reports when conditions associated with acute cardiac ischemia are detected, including conditions that would lead to an acute myocardial infarction or unstable angina. The device 10 extracts and evaluates subtle, globally-distributed features from a patient's ECG. The extracted global features are then classified to determine whether an acute cardiac ischemic condition has been detected. In a further embodiment of the present invention, the device 10 also derives local features from a patient and classifies both the global and local features to determine whether an acute cardiac ischemic condition has been detected.

Figure 4:
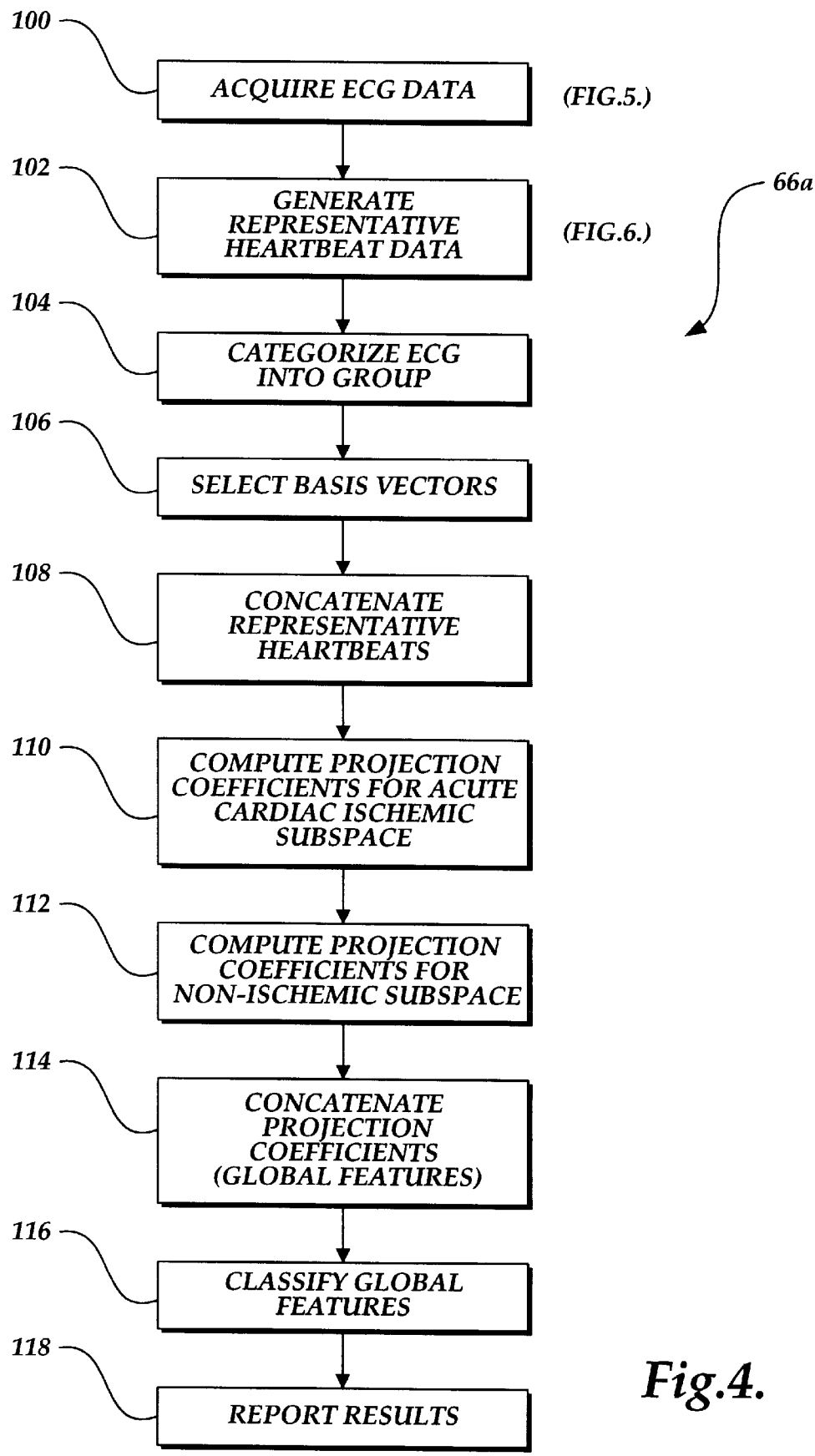
FIG. 4 is a flow diagram illustrating an acute cardiac ischemia detection process conducted by the device shown in FIGS. 2 and 3 which detects acute cardiac ischemic events by classifying global features derived from a patient's ECG.

FIG. 4 is a flow diagram illustrating a version of an acute cardiac ischemia detection process 66a that determines detects acute cardiac ischemia based on classifying global features. The detection process includes both the extraction of global features in blocks 100–114 and the classification of the global features in block 116. The detection process begins in a block 100 with the acquisition of ECG data from a patient. As illustrated more fully in FIG. 5, ECG data acquisition begins in a block 122 with attaching electrodes, such as sensing electrodes 12, 14, 16, 18, 20, 22, 24, 26, 28, and 30 to a patient 40. Once the electrodes are attached to a patient, the user of the device 10 initiates ECG data acquisition in a block 124 by initiating an input device 68, e.g., by pressing an ANALYZE button on the device. Alternatively, the device 10 could automatically initiate ECG data acquisition, e.g., upon expiration of a predetermined period of time counted by a timer that is started upon deployment or activation of the device 10. For a period of time thereafter, the voltage signals sensed by the electrodes are amplified in a block 126, filtered in a block 128, and converted to digital ECG data in a block 130 as discussed earlier in reference to the preamplifier 50 and the A/D converter 60 shown in FIG. 3. The ECG data is subsequently stored in a block 132 in the memory 64 of the device 10.

The period of time in which ECG data is acquired in block 100 of FIG. 4 is long enough to obtain sufficient, high-quality data representative of one or more heartbeats. In one actual embodiment of the present invention, about ten seconds of ECG data is acquired. This period of time may be increased or decreased depending on factors that affect the quality of the data acquired, including the quality of the connection between the electrodes and the patient, whether the patient is moving, and whether significant electromagnetic noise is present. Accordingly, depending on various factors, the period time for ECG acquisition may be increased or decreased to, for example, twenty seconds or five seconds, and still be considered an equivalent of about ten seconds of data for purposes of the subsequent processing discussed below.

After acquiring a patient's ECG data in block 100, the device 10 analyzes the ECG data and generates representative heartbeat data for each available lead in a block 102. Preferably, the representative heartbeat data represents an atrially stimulated heartbeat that is common for the lead and is typically characterized by a high signal-to-noise ratio. If the acquired ECG data is of sufficient high quality, a single beat may be used for the representative heartbeat data. In most cases, however, it is preferable to combine two or more heartbeats on each lead to generate representative heartbeat data for the lead.

Figure 1:
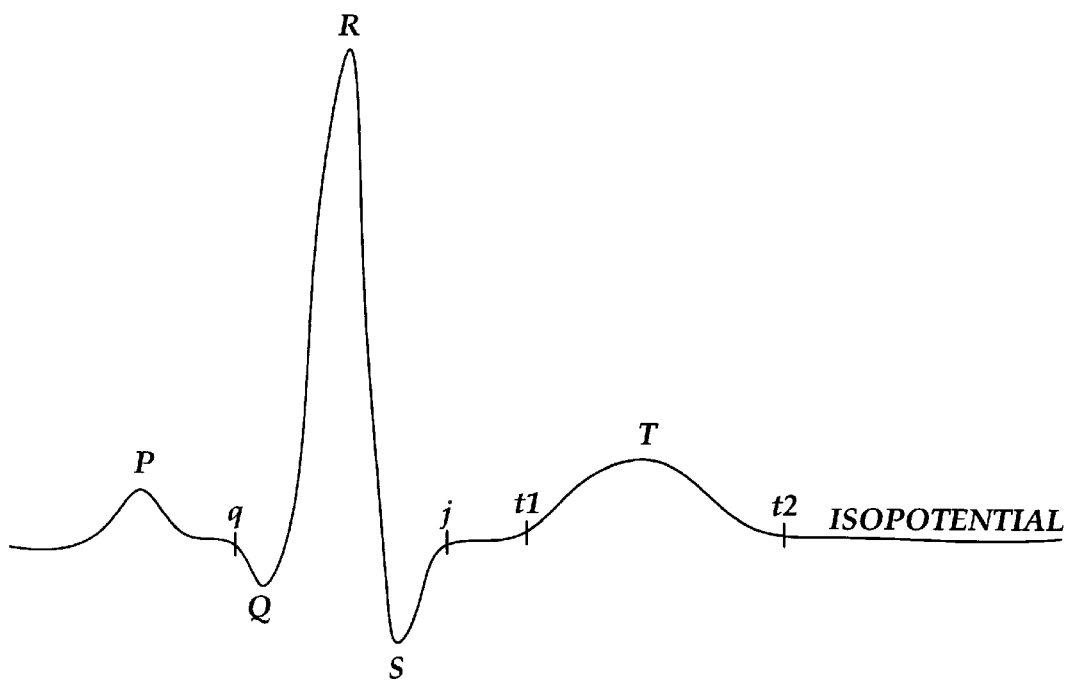
FIG. 1 illustrates an example of an ECG waveform corresponding to a single heartbeat.
Figure 6:
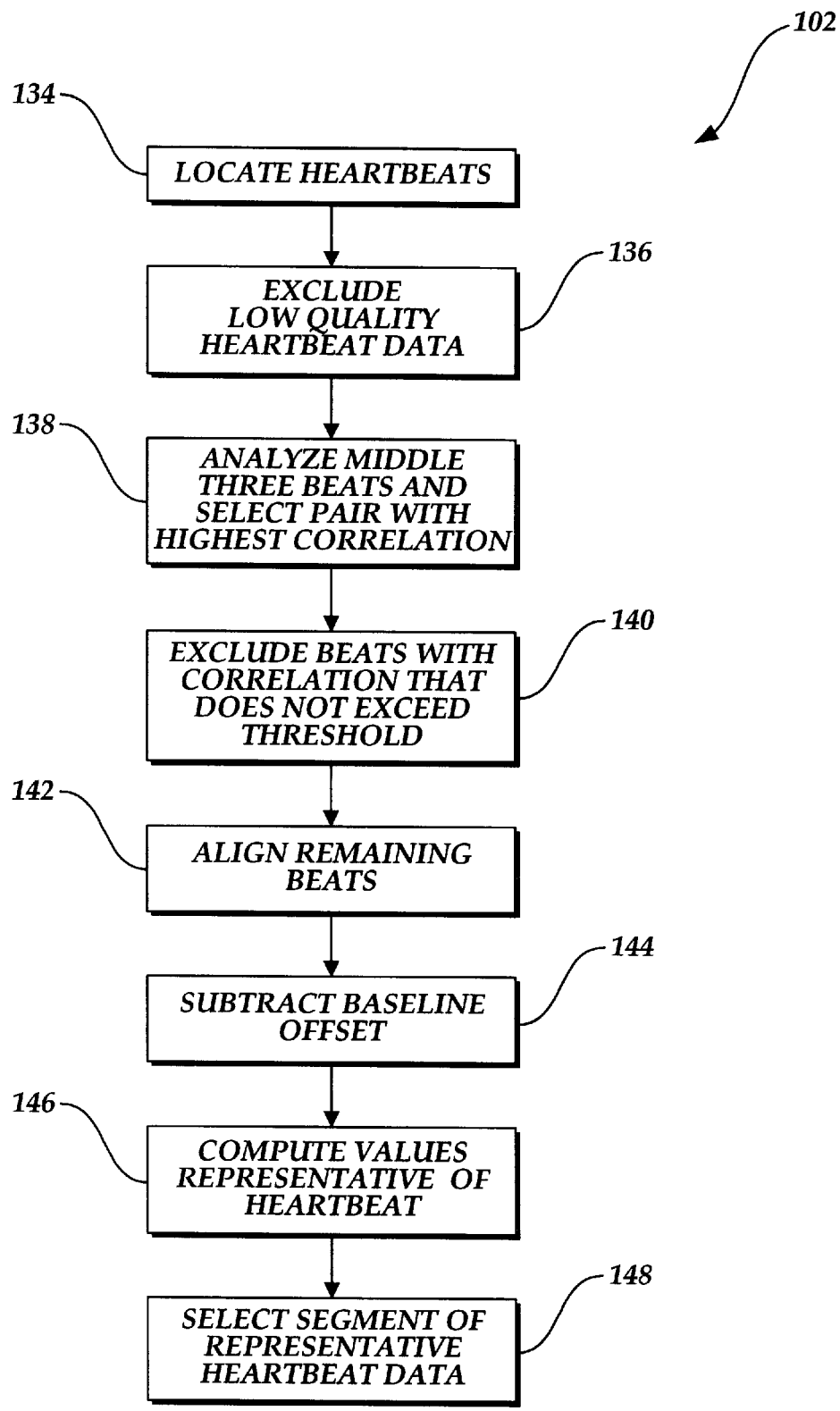
FIG. 6 is a flow diagram illustrating a process used to generate representative heartbeat data for the acute cardiac ischemia detection process shown in FIG. 4.

FIG. 6 illustrates in more detail a process for generating representative heartbeat data suitable for use in the present invention. In the process shown, multiple heartbeats on a lead are used to generate the representative heartbeat data for the lead. The device 10 first locates the heartbeats on each lead in a block 134. In that regard, heartbeats may be located by detecting the dominant feature of the QRS complexes, i.e., the R waves (see FIG. 1), of each heartbeat. Because the quality of the representative heartbeat data is improved by selecting and using only high quality ECG data, the raw ECG data is analyzed in a block 136 to exclude low quality heartbeat data. For example, heartbeat data that exhibits significant noise content (e.g., data with energy values greater than one standard deviation away from the mean of the QRS energy values measured, for example, by a sum of squared values) is excluded in block 136 from further consideration for generating a representative heartbeat. Of the retained heartbeat data, the middle three heartbeats (middle in a temporal sense) are analyzed and two of the three heartbeats that have a highest pairwise cross-correlation are selected in a block 138 for further consideration. The non-selected third heartbeat is excluded from further consideration.

The retained heartbeats are then individually compared with the first heartbeat of the pair selected above. Specifically, a cross-correlation value is determined for each of the QRS complexes of the remaining heartbeats with respect to the first beat of the selected pair. Those heartbeats having a correlation value greater than a specified threshold value (e.g., 0.9 out of a perfect 1.0) are retained. The heartbeats having a lower correlation value are excluded in a block 140 from further consideration for generating a representative heartbeat. The heartbeats retained are used in generating a representative heartbeat for the lead being analyzed.

To generate a representative heartbeat for the lead, the waveforms of the retained heartbeats are aligned in a block 142 by matching up waveform features such as the R wave peak, preferably according to the maximum cross-correlation of data samples in the retained heartbeats. Further, a baseline offset calculated for each beat is subtracted in a block 144 from the data samples in each retained heartbeat. The baseline offset is the amount that the data samples in a heartbeat exceed a selected reference level. In an actual embodiment of the invention, the baseline offset is estimated as the mean of 48 milliseconds of ECG data taken from an 88 millisecond mark to a 40 millisecond mark prior to the QRS peak sample (e.g., if the QRS peak was located at the 100 millisecond mark, the estimated baseline offset was the mean of the samples from the 12 millisecond mark to the 60 millisecond mark). It is appreciated that more or less ECG data may be used, or the timing of the ECG segment used may be shifted, in calculating a baseline offset.

Next, in a block 146, a set of values representative of an average heartbeat for each lead is computed from the retained heartbeat data. In an actual embodiment of the invention, the representative heartbeat data is generated by calculating a sample-by-sample average of the retained heartbeats. Nevertheless, it is understood that a wide variety of mathematical operations may be used instead of averaging. For example, representative heartbeat data may be calculated from a sample-by-sample mean, mode, weighted mean (using weighing coefficients), or trimmed mean (i.e., calculate a mean from a set of values that excludes values that are too large or too small), or median.

Before the resulting representative heartbeat data is subjected to further evaluation, it may be advantageous to reduce the amount of data being evaluated. In that regard, data samples in a segment of the representative heartbeat are selected in a block 148 to represent the ECG information of particular interest. In one actual embodiment of the present invention, a 480 millisecond segment of representative heartbeat data for each available lead is selected beginning at an 8 millisecond mark before each representative beat's QRS peak. Data outside the selected segment is excluded from the further processing and evaluation performed. In reducing the amount of data being evaluated, it is appreciated that a segment of ECG data longer or shorter than 480 milliseconds may be selected. The beginning mark may also be adjusted earlier or later in the sequence of ECG data.

While the process shown in FIG. 6 is used to generate representative heartbeat data in one actual embodiment of the invention, it should be understood that other ones of the many known procedures for generating representative heartbeats can be used. For example, the methods of representative heartbeat generation used in the LIFEPAK® 11 or LIFEPAK® 12 defibrillators manufactured by Physio-Control Corporation of Redmond, Wash., may be used, if desired.

Returning again to FIG. 4, once representative heartbeat data is generated for each of the available leads in block 102, in accordance with the present invention, the data is subjected to a global classification evaluation in blocks 104–116. As will be better understood from the discussion below, a global classification evaluation involves concatenating the representative heartbeat data produced on the available leads, extracting global features from the concatenated representative heartbeat data, and determining whether the global features are in a class indicative of acute cardiac ischemia. More specifically, as will be discussed more fully below, a global classification evaluation involves mathematically projecting a concatenated vector of representative heartbeat data onto predetermined basis vectors that define an acute cardiac ischemic ECG subspace and onto predetermined basis vectors that define a non-ischemic ECG subspace. The resulting projection coefficients are the global features that are classified to determine whether an acute cardiac ischemic condition is detected.

While a 480 millisecond segment of representative heartbeat data is selected in an actual embodiment of the invention in block 148 (FIG. 6), it is again noted that any segment length (preferably containing, at least, the QRST portions of the ECG) may be used. Nevertheless, as will be better understood from the discussion below, a fixed number of samples in a representative heartbeat must be set a priori during a preprocessing training phase for the later performed global classification evaluation of the present invention. The length of the basis vectors determined during the training phase and later used in the global classification evaluation depends on both the number of data samples in each representative heartbeat and the number of available leads used from the ECGs of a training population of patients in the preprocessing training phase.

Prior to discussing the global classification evaluation illustrated in blocks 104–116 of FIG. 4, a brief discussion of some concepts underlying the evaluation is provided. A description of the preprocessing training phase required to derive the basis vectors is also provided.

The global classification evaluation shown in FIG. 4 is based on the concept that a series of numbers can be viewed as coefficients of a vector that defines a point in a multidimensional signal space. In the case of the present invention, this means that a series of ECG data points in a patient's representative heartbeat may be viewed as coefficients of a vector defining a point in a multidimensional ECG signal space. The number of dimensions in the ECG signal space is determined by the number of data points in the patient's representative heartbeat data. In a similar manner, a series of global features derived from a patient's ECG according to the present invention may be viewed as coefficients of a vector defining a point in a multidimensional feature space. The number of dimensions in the feature space is determined by the number of global features derived from the patient's ECG. It should be understood that the ECG signal space and the feature space are completely different conceptual spaces, though in regard to this invention they are related by virtue of the projecting operation described later in reference to blocks 110 and 112 of FIG. 4.

For purposes of discussion herein, patients in a training population of patients known to have acute cardiac ischemia are referred to as ischemic training patients or an ischemic training population. Likewise, patients in a training population of patients known to not have acute cardiac ischemia are referred to as non-ischemic training patients or a non-ischemic training population. Sets of global features derived from the ECG data of ischemic training patients may be plotted as points defining an "ischemic" region of a feature space. In a similar fashion, sets of global features derived from the ECG data of non-ischemic training patients may be plotted as points defining a "non-ischemic" region of the feature space. According to the present invention, if a set of global features derived from the ECG data of a patient under current evaluation defines a point closer to the ischemic region than the non-ischemic region, a diagnosis of acute cardiac ischemia is reported. The threshold of "closeness" for making such a diagnosis is adjustable, thus providing the device with an adjustable sensitivity/specificity tradeoff, as will be discussed in more detail below.

Within the ECG signal space (which, as noted, is different than the feature space), ECG data obtained from ischemic training patients is viewed as defining an ischemic ECG subspace. Likewise, ECG data obtained from non-ischemic training patients is viewed as defining a non-ischemic ECG subspace. The ischemic and non-ischemic ECG subspaces may be succinctly characterized by mathematical basis vectors derived in a training phase (discussed below). The basis vectors are stored as preprocessed parameters 67 in memory 64 of the device 10. As will be discussed later in greater detail, the basis vectors are used in blocks 110 and 112 of FIG. 4 to derive the projection coefficients (i.e., global features) of the patient under current evaluation.

Before deriving a set of basis vectors for characterizing each of the ischemic and non-ischemic ECG subspaces, the quality of this characterization may be enhanced by dividing the ischemic and non-ischemic training populations into smaller groups according to a selected characteristic. Sets of basis vectors (ischemic and non-ischemic) are then derived for each group from the ECG data of the training patients in the group. However, dividing the training populations into groups is not required.

In one embodiment of the invention, the training populations are divided into groups according to locations of ischemic conditions (e.g., anterior, inferior, and other). The selected characteristic used to divide the training populations is the identity of the lead with the greatest ST elevation. It has been found that the identity of the lead with the greatest ST elevation is generally indicative of the location of an acute cardiac ischemic condition. Accordingly, each patient in the ischemic and non-ischemic training populations is assigned to an "inferior," "anterior," or "other" group based on the patient's ST elevation measures.

While in this regard the ST elevation on each individual lead of a patient may be separately evaluated, in an actual embodiment of the present invention, three composite ST elevation measures $\{u_1, u_2, u_3\}$ are calculated and used to group the patients in the training populations. The measure $u_1$ is the mean of the ST elevation on leads II and aVF. The measure $u_2$ is the mean of the ST elevation on leads I, aVL, V6. Lastly, the measure $u_3$ is the mean of the ST elevation on leads V2, V3, and V4. If the measure $u_1$ for a given patient is the greatest of the three composite measures, the patient is assigned to the "inferior" group. If the measure $u_2$ is greatest, the patient is assigned to the "other" group (which includes lateral and septal ischemic locations). If the measure $u_3$ is greatest, the patient is assigned to the "anterior" group.

It is appreciated that alternative groups may be defined according to other selected characteristics. For example, local features other than ST elevation, such as T wave amplitude, QRS area measures, etc., and patient clinical information (e.g., age, sex, etc.), may be used to divide the training populations into groups. Alternatively, selected local features may be classified first to produce a preliminary determination of ischemia that is used as a basis for dividing the training populations. Local features and classification methods suitable for producing preliminary determinations in this regard are described in more detail below in reference to FIGS. 13 and 14. It is further appreciated that basis vectors may be derived for each of the training populations as a whole, without dividing the training populations into groups.

Figure 7:
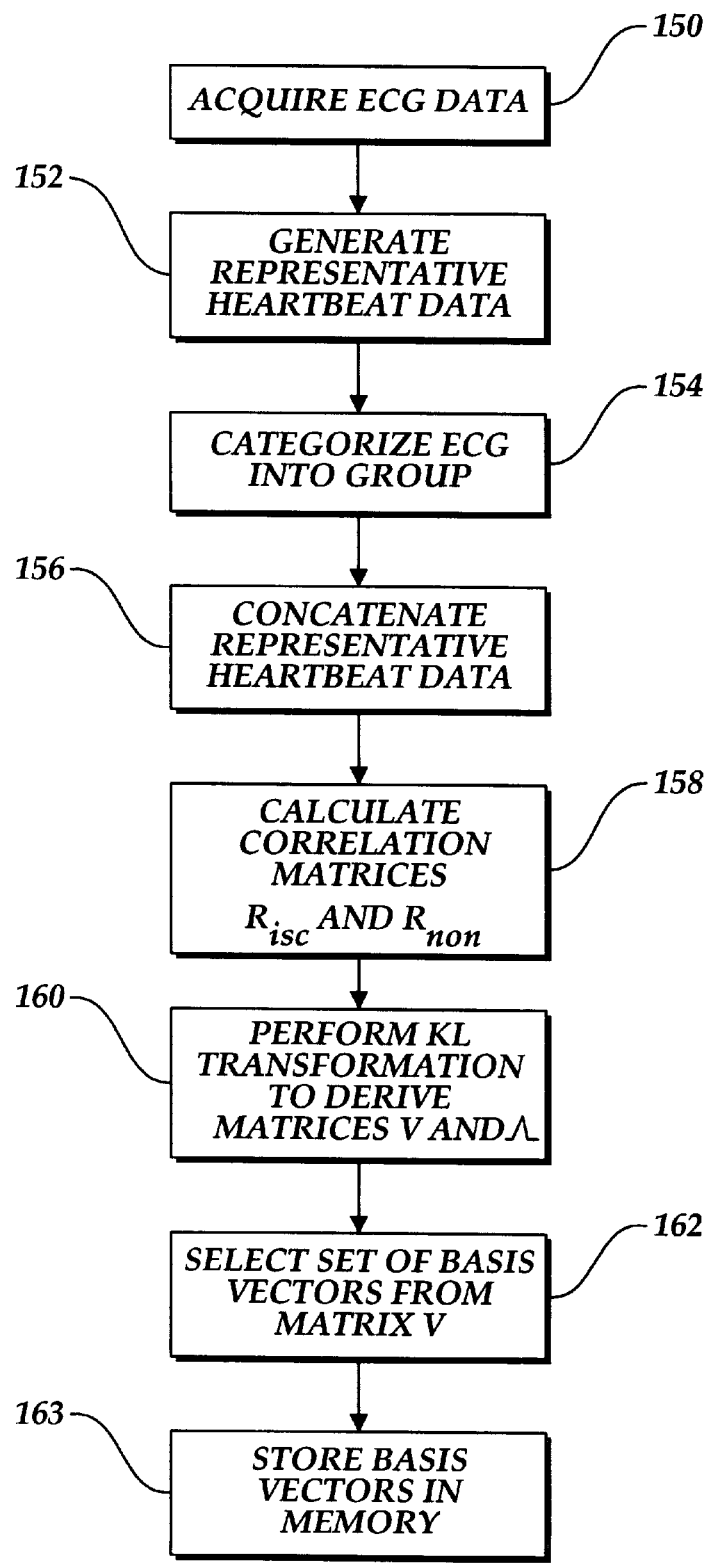
FIG. 7 is a flow diagram illustrating a process performed during a training phase to derive a set of basis vectors used by the acute cardiac ischemia detection process shown in FIG. 4 to detect acute cardiac ischemia.

For the sets of ischemic and non-ischemic training patients in each group (or for each training population as a whole if grouping is not performed), a set of basis vectors is derived. FIG. 7 illustrates in more detail a process for deriving basis vectors. In a block 150 in FIG. 7, ECG data is acquired from each of the patients in the ischemic and non-ischemic training populations. The ECG data may be acquired using a conventional 12-lead ECG device or a device 10 such as that shown in FIGS. 2 and 3, in the manner earlier described in reference to FIG. 5. After acquiring ECG data from each of the training patients, representative heartbeat data is generated from the ECG data in a manner as earlier described in reference to FIG. 6. More specifically, for each patient in the training populations, representative heartbeat data is generated from ECG data collected, for example, on each of twelve leads labeled I, II, III, aVR, aVL, aVF, V1, V2, V3, V4, V5 and V6. These leads are depicted generally in FIG. 9 in which dots are used to indicate a series of numbers that, in this regard, forms the representative heartbeat data.

Assuming for the sake of discussion that the training populations are divided into groups according to locations of acute cardiac ischemia as described above, the ECG of each patient in the training populations is categorized into a group in a block 154 according to the ST elevation measures calculated for each patient. Next, in a block 156 the representative heartbeat data generated for each patient in each group is concatenated to form a representative heartbeat vector "$\underline{x}$". A concatenated representative heartbeat vector $\underline{x}$ includes the representative heartbeat data of a first lead (e.g., lead I), immediately followed by the representative heartbeat data of a second lead (e.g., lead II), a third lead (e.g., lead III), a fourth lead (e.g., lead aVR), and so on. A concatenated representative heartbeat vector $\underline{x}$ is depicted generally in FIG. 10, with vertical dashed partitions between the lead data shown for illustrative purposes only. It is to be understood that alternative embodiments of the invention may use a different (and/or smaller) combination of leads than that shown in FIGS. 9 and 10.

In an embodiment of the invention where twelve leads of ECG data are acquired at a sampling rate of 500 samples per second, and a 480 millisecond segment of data per representative heartbeat is used, each lead (e.g., the leads shown in FIG. 9) includes 240 samples of heartbeat data, thus producing a concatenated representative heartbeat vector $\underline{x}$ (as shown in FIG. 10) having 2,880 samples of heartbeat data. A concatenated representative heartbeat vector $\underline{x}$ is thus obtained for each of the patients in the respective training populations.

For the ischemic and non-ischemic sets of patients in each group, the patients' concatenated heartbeat vectors $\underline{x}$ are combined together in a block 158 in FIG. 7 to calculate correlation matrices $R_{isc}$ and $R_{non}$ using the following general equation:

$$R = \frac{1}{N}\sum_{i=1}^{N}(x_i x_i^T) \qquad (1)$$

The values in matrix R of Equation (1) are normalized according to the total number of patients "N" whose concatenated heartbeat vectors x were used. Thus, using Equation (1), a correlation matrix $R_{isc}$ is calculated for the ischemic patients in each group, and a correlation matrix $R_{non}$ is calculated for the non-ischemic patients in each group.

For each correlation matrix R (regardless of whether the training populations are divided into groups), a Karhunen-Loeve (KL) transformation is performed in a block 160 to derive a matrix V and a matrix Λ that satisfies the following general equation:

$$R = V\Lambda V^T \quad (2)$$

A matrix V and a matrix Λ are illustrated generally in FIGS. 11A and 11B, respectively. The columns of the matrix V are mutually orthogonal basis vectors that collectively define the ECG subspace of the concatenated heartbeat vectors x used in Equation (1) to form the correlation matrix R. The matrix Λ in FIG. 11B is a matrix whose diagonal consists of eigenvalues corresponding to the correlation matrix R and are ordered from largest to smallest in value along the diagonal. Likewise, the basis vectors (i.e., the columns in matrix V) are eigenvectors that correspond to the eigenvalues of the correlation matrix R. If the concatenated heartbeat vectors x have 2,880 samples each, then the dimension of both matrix V and matrix Λ, as well as correlation matrix R, is 2880×2880.

Because the eigenvalues in matrix Λ are ordered from largest to smallest value along the diagonal, the initial columns of matrix V, which correspond with the eigenvalues of greatest value, are more significant in terms of signal synthesis than the latter columns of matrix V, which correspond with smaller eigenvalues. A set of basis vectors is selected in a block 162 of FIG. 7 (e.g., the first ten columns of matrix V labeled BV1, BV2, BV3, BV4, . . . , BV10 in FIG. 11A) for later use as preprocessed parameters 67 in computing the current patient's global features. Although signal representation error theoretically decreases with the inclusion of additional basis vectors, experience thus far has indicated that using more than ten basis vectors does not markedly improve classification performance in the present invention. Moreover, the basis vectors corresponding to smaller eigenvalues (i.e., the latter columns of matrix V) that are not used are more likely to be affected by noise.

It will be appreciated that other sets of columns, or basis vectors, may be selected from matrix V. For example, instead of using the first ten columns of matrix V, a set of basis vectors including the first, third, fifth, and seventh columns may be used. Basis vectors beyond the first ten columns may also be selected An optimal set of basis vectors may be determined empirically for the ischemic and non-ischemic training patients in each group. If the training populations are not divided into groups, a single paired set of basis vectors (i.e., a set of ischemic basis vectors and a set of non-ischemic basis vectors) may be used to represent the ECG subspaces of the ischemic population and the non-ischemic population as a whole. The selected vectors are then stored in a block 163 as preprocessed parameters 67 in memory 64 for later use in deriving global features from the ECG of a patient undergoing evaluation.

Returning now to FIG. 4, given a defined number of groups and a paired set of ischemic and non-ischemic basis vectors associated with each group, the ECG of a patient under current evaluation is categorized in a block 104 into the group to which it best pertains. As part of categorizing the patient's ECG, composite ST elevation measures $u_1$, $u_2$, and $u_3$ are calculated for the current patient as they are described above for the training populations. The current patient's ECG is categorized into the "inferior" group if the measure $u_1$ is greatest. If the measure $u_3$ is greatest, the patient's ECG is categorized into the "anterior" group. If the measure $u_2$ is greatest, the patient's ECG is categorized into the "other" group.

Once a patient's ECG is categorized into a particular group in block 104, the paired set of basis vectors associated with the group are selected in a block 106 from the preprocessed parameters 67 in memory 64 for use in evaluating the patient's ECG. The patient's representative heartbeat data for each of the available leads is then concatenated in a block 108 to form a concatenated heartbeat vector "x", in a manner as described earlier for the patients in the training populations. Next, in blocks 110 and 112 of FIG. 4, the patient's concatenated heartbeat vector x is mathematically projected onto the basis vectors selected in block 106. Broadly stated, the projecting operation (described in more detail below) results in a number of projection coefficients that are used as global features of the patient's ECG. The number of global features extracted from the patient's ECG corresponds to the number of basis vectors used in the projecting operation.

Figure 12A:
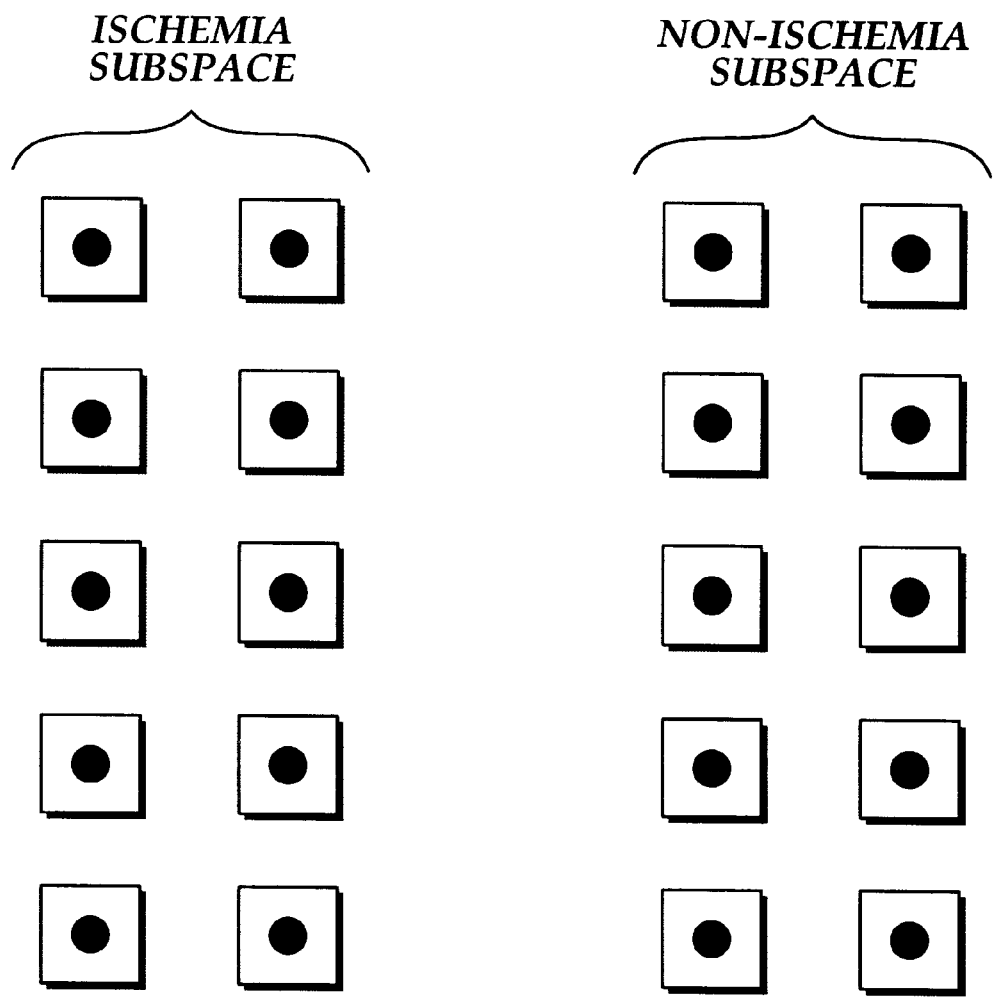
FIG. 12A is a pictorial diagram of twenty projection coefficients ("global features") calculated during the acute cardiac ischemia detection process shown in FIG. 4 by projecting a patient's concatenated representative heartbeat vector $\underline{x}$, as shown in FIG. 10, onto ten basis vectors spanning acute cardiac ischemia ECG subspace and ten basis vectors spanning non-ischemia ECG subspace, the basis vectors being determined beforehand as shown in FIG. 7.
Figure 12B:
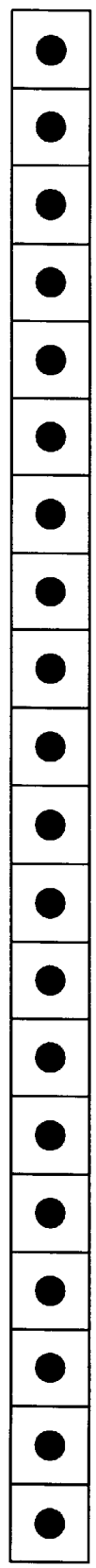
FIG. 12B is a pictorial diagram of a concatenated global feature vector $\underline{f}$ that includes the twenty global features depicted in FIG. 12A.

More specifically, the projecting operation involves projecting the patient's concatenated heartbeat vector x onto the basis vectors defining an acute cardiac ischemic ECG subspace in block 110 by computing an inner product of the vector x with each of the ischemic basis vectors. The patient's concatenated heartbeat vector x is also projected onto the basis vectors defining the corresponding non-ischemic ECG subspace in block 112 by computing an inner product of the vector x with each of the non-ischemic basis vectors. If, for example, ten basis vectors are used to characterize each of the ischemic and non-ischemic ECG subspaces, the projecting operation results in a total of twenty scalar projection coefficients that are used as global features, as generally depicted in FIG. 12A. Once the patient's concatenated heartbeat vector x is projected onto the ischemic and non-ischemic basis vectors in blocks 110 and 112 of FIG. 4 (i.e., once the global features are calculated), the global features are concatenated in a block 114 into a single global feature vector "f", as generally depicted in FIG. 12B.

Next, in a block 116, the global features derived from the current patient's ECG data are classified to determine whether acute cardiac ischemia is detected. The classifier in block 116 evaluates the global features of the current patient relative to representative global features previously derived during a training phase from patients in the ischemic and non-ischemic training populations. In one actual embodiment of the present invention, a Gaussian classifier is used to compare the current patient's global features with a set of mean global features normalized by covariances previously derived from the training populations. If the current patient's global features are "closer" to the normalized mean global features of the ischemic population than the non-ischemic population (hence, in a graphical sense, define a point "closer" to the ischemic region than the non-ischemic region of the feature space), a report of acute cardiac ischemia is produced.

In order to understand the classifier in block 116, it is necessary to understand the preprocessing performed to train the classifier. During the training phase in which the ischemic and non-ischemic basis vectors are derived, a vector of mean global features "m" and a covariance matrix "C" are calculated for each set of ischemic training patients and non-ischemic training patients. In other words, a vector $m_{isc}$ and matrix $C_{isc}$, and a vector $m_{non}$ and matrix $C_{non}$, are calculated for each group (as described below). The vectors of mean global features $\underline{m}_{isc}$ and $\underline{m}_{non}$, and covariance matrices $C_{isc}$ and $C_{non}$, are used in classifying the current patient's global features. The preprocessing performed during the training phase to train the classifier in this regard is shown in more detail in FIG. 8.

Figure 8:
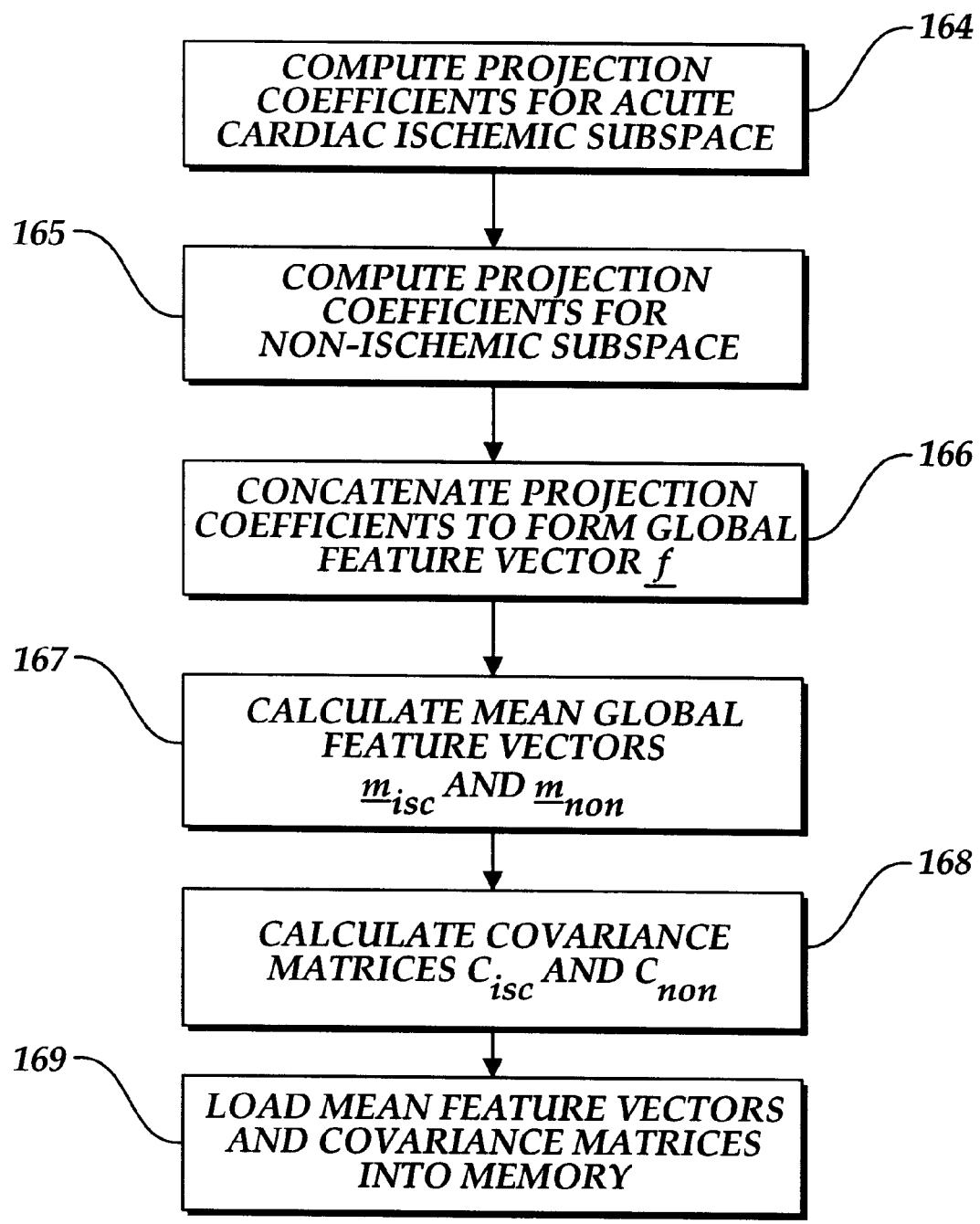
FIG. 8 is a flow diagram illustrating a process performed during the training phase to derive a set of classifier parameters used by the acute cardiac ischemia detection process shown in FIG. 4.

In blocks 164 and 165 of FIG. 8, global features for each patient in each group of training patients are calculated using the basis vectors derived for the group. More specifically, the concatenated representative heartbeat vector $\underline{x}$ produced in block 156 (FIG. 7) for each training patient is mathematically projected onto the ischemic and non-ischemic basis vectors for the training patient's group in the manner as described earlier in reference to blocks 110 and 112 of FIG. 4. Next, in a block 166, the resulting ischemic and non-ischemic projection coefficients for each training patient are concatenated to form a global feature vector f in the manner as earlier described and generally depicted in FIG. 12B.

Mean feature vectors $\underline{m}_{isc}$ and $\underline{m}_{non}$ are then calculated in a block 167 for each group by computing a feature-by-feature mean of the concatenated global feature vectors $\underline{f}$ produced from the respective ischemic and non-ischemic patients in each group. In a configuration where ten basis vectors are used to characterize each of the ischemic and non-ischemic ECG subspaces, the concatenated global feature vector $\underline{f}$ for the patients in the training populations, and thus the mean feature vectors $\underline{m}_{isc}$ and $\underline{m}_{non}$ for each group, will include twenty values.

In addition to calculating mean feature vectors $\underline{m}_{ics}$ and $\underline{m}_{non}$ in block 167, covariance matrices $C_{isc}$ and $C_{non}$ are calculated in block 168 for the respective ischemic and non-ischemic training patients in each group. Generally speaking, a covariance matrix C contains the statistical covariance of the global feature vectors $\underline{f}$ of a set of N number of patients, and is calculated as follows:

$$C = \frac{1}{N} \sum_{i=1}^{N} ((\underline{f}_i - \underline{m})(\underline{f}_i - \underline{m})^T) \quad (3)$$

The covariance matrix C provides an indication of how widely dispersed the global features of the set of patients are from the calculated mean global features for the same set of patients. The mean feature vector $\underline{m}$ and the covariance matrix C thus calculated for each of the ischemic and non-ischemic sets of patients in each group are stored in a block 169 as preprocessed parameters 67 in memory 64 (FIG. 3) for later use in classifying the current patient's global features.

Returning to FIG. 4, according to one implementation of the invention, the Gaussian classifier in block 116 evaluates the current patient's global feature vector $\underline{f}$ with respect to the mean global feature vectors $\underline{m}_{ics}$ and $\underline{m}_{non}$, and covariance matrices $C_{isc}$ and $C_{non}$ according to the following equation:

$$d = \sqrt{(\underline{f}-\underline{m})^T C^{-1} (\underline{f}-\underline{m})} \quad (4)$$

The quantity "d" computed from Equation (4) reflects the distance between the patient's global feature vector $\underline{f}$ and a mean global feature vector $\underline{m}$ weighted by a covariance matrix C. Accordingly, a quantity $d_{isc}$ reflects the distance between a patient's global feature vector $\underline{f}$ and the mean global feature vector $\underline{m}_{isc}$ weighted by a covariance matrix $C_{isc}$ for the acute cardiac ischemia ECG subspace. Similarly, a quantity $d_{non}$ reflects the distance between a patient's global feature vector $\underline{f}$ and the mean global feature vector $\underline{m}_{non}$ weighted by the covariance matrix $C_{non}$ for the non-ischemia ECG subspace. The Gaussian classifier in block 116 then compares the quantities disc and $d_{non}$, and if disc is less than $d_{non}$, an acute cardiac ischemic condition is detected and reported. It is appreciated that alternative distance metrics may be used for comparing a patient's global feature vector $\underline{f}$ with a mean global feature vector $\underline{m}$ to produce other quantities for "d."

The covariance matrix C is inverted in Equation (4) so that if a mean global feature has a corresponding high covariance, any deviation of the patient's respective global feature from the mean global feature is not weighted as greatly as a situation wherein the respective mean global feature has a low covariance. Thus, if a particular global feature of the patient deviates significantly from a corresponding mean global feature having a low covariance, greater attention is drawn to the patient's deviation on that feature by giving greater weight to the resultant value.

For purposes of discussion herein, it is presumed that the Gaussian classifier in block 116 uses a distance metric that reports the detection of acute cardiac ischemia if $d_{isc}$ is less than $d_{non}$. In other words, if $d_{non} > d_{isc}$, a detection of acute cardiac ischemia is reported. From the foregoing, it follows that if $d_{non} - d_{isc} > 0$, a detection of acute cardiac ischemia is reported. The computed quantity on the left side of the latter inequality is called a classification statistic. The value "0" on the right side of the latter inequality is a decision threshold against which the classification statistic is compared. More generally stated, if $d_{non} - d_{isc} > t$, where "t" is the decision threshold, acute cardiac ischemia is reported. As will be discussed below, the sensitivity and specificity of the device 10 may be adjusted by varying the threshold "t".

While a Gaussian classifier has been described above, it is appreciated that alternative statistical classifiers may be used to evaluate a patient's global features. Such alternative statistical classifiers may use, for example, the techniques of logistic regression, k-nearest neighbor procedures, discriminate analysis, as well as neural network approaches. The output of a statistical classifier is a quantity that is typically compared to a numerical threshold to arrive at a final binary decision, e.g., whether or not acute cardiac ischemia is present. For an expanded description of suitable alternative statistical classifiers, see R. Duda and P. Hart, *Pattern Classification and Scene Analysis* (1973), published by John Wiley & Sons, New York, which is incorporated herein by reference.

As noted, the outcome of the evaluation made by the classifier in block 116 is reported to the user of the device in a block 118. As a further aspect of the invention, if the training populations are divided into groups according to ischemia location, the reported outcome may also identify the location of the ischemic condition (if acute cardiac ischemia is detected) based on the group into which the patient's ECG was categorized. Knowing whether a detected ischemic condition is at an inferior, anterior, or other location may assist a caregiver in treating the ischemic condition.

Although the acute cardiac ischemia detection process 66a described above involves projecting a patient's concatenated heartbeat vector $\underline{x}$ onto basis vectors that collectively define both an acute cardiac ischemic ECG subspace and a non-ischemic ECG subspace, it should be understood that, alternatively, the patient's concatenated heartbeat vector $\underline{x}$ may be projected onto one or more basis vectors that define only an acute cardiac ischemic ECG subspace, i.e., without projection onto any basis vectors that define a non-ischemic ECG subspace. In that regard, only "ischemic" projection coefficients (i.e., ischemic global features) are produced and classified.

A classifier for classifying only ischemic global features does not need to be any different in structure than a classifier that classifies both ischemic and non-ischemic global features, as described above in reference to block 116 (FIG. 4). The only difference is the number of global features used in the classification and the training of the classifier performed beforehand in a training phase.

In the training phase, the basis vectors defining an acute cardiac ischemic ECG subspace are derived from the ischemic training population as described earlier in reference to FIG. 7. Then, for each training patient in both the ischemic and non-ischemic training populations, ischemic global features are calculated using the derived ischemic basis vectors in a manner as described earlier in reference to block 164 in FIG. 8. The ischemic global features for each patient (ischemic and non-ischemic) are concatenated into a global feature vector $\underline{f}$ as described earlier in reference to block 166.

Mean feature vectors $\underline{m}_{isc}$ and $\underline{m}_{non}$ and covariance matrices $C_{isc}$ and $C_{non}$ are then calculated in a manner as described in reference to blocks 167 and 168. The vectors $\underline{m}_{isc}$ and $\underline{m}_{non}$ and matrices $C_{isc}$ and $C_{non}$, are stored as preprocessed parameters 67 in the memory 64 for later use in classifying the ischemic global features of the current patient as discussed in reference to block 116.

Alternatively, the patient's concatenated representative heartbeat vector $\underline{x}$ may be projected onto one or more basis vectors that define only a non-ischemic ECG subspace, i.e., without projection onto any basis vectors that define an acute cardiac ischemic ECG subspace. In that regard, only "non-ischemic" projection coefficients (i.e., non-ischemic global features) are produced and classified. The same procedures discussed above for training the classifier are used, except the basis vectors that define a non-ischemic ECG subspace are used instead of the ischemic basis vectors. Furthermore, as discussed earlier, if the training populations are divided into groups according to ischemia location, the reported outcome (if ischemia is detected) may also identify the location of the ischemic condition.

Figure 13:
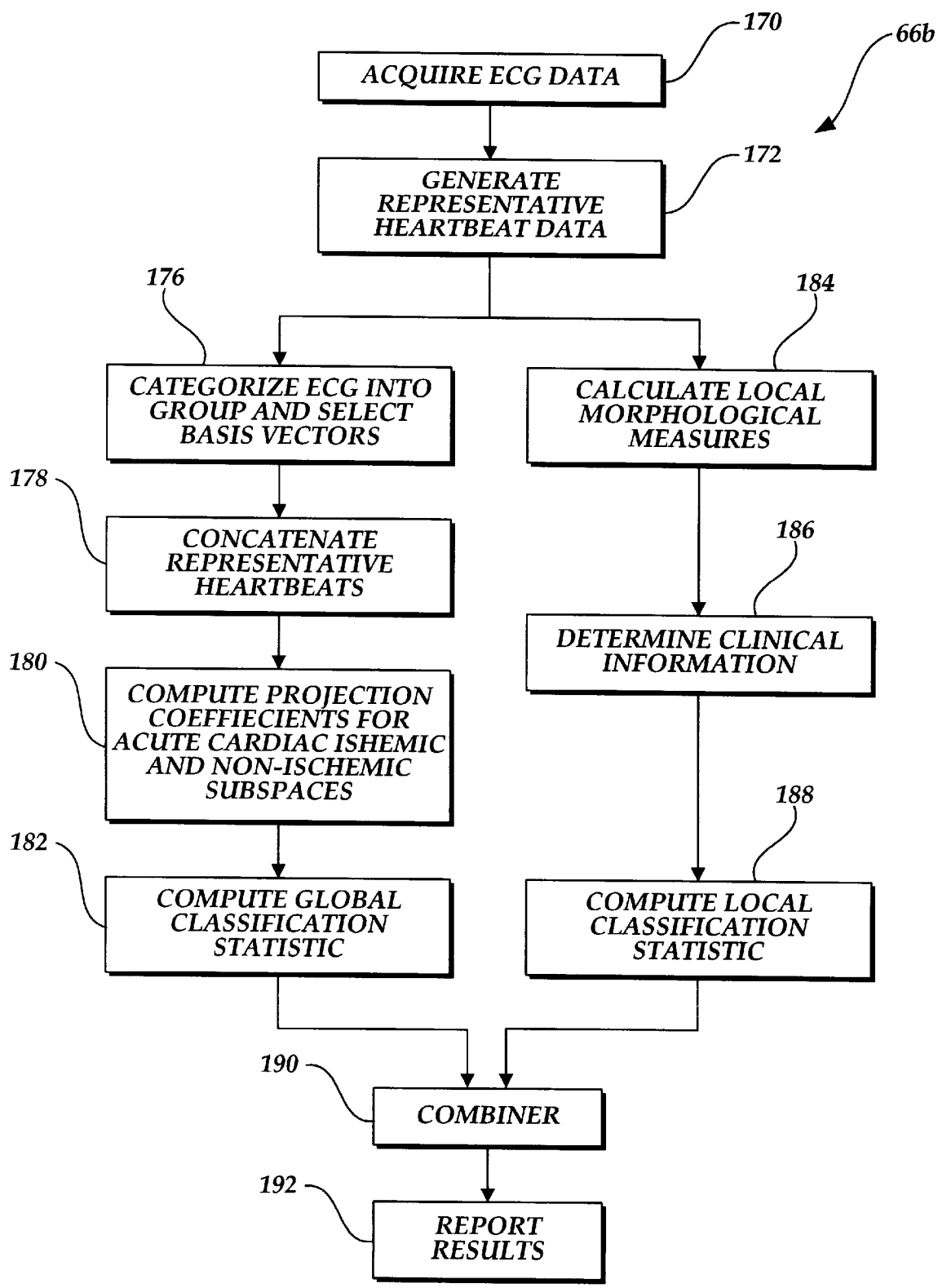
FIG. 13 is a flow diagram illustrating an alternative acute cardiac ischemia detection process conducted by the device shown in FIGS. 2 and 3 which detects acute cardiac ischemic events by separately classifying global and local features derived from a patient and classifying the results of the separate classifications.

FIG. 13 is a flow diagram illustrating another version of an acute cardiac ischemia detection process 66b formed in accordance with the present invention. In this version, local features are derived from a patient and classified along with global features to diagnose acute cardiac ischemia. Local features derived from a patient include local morphological measures taken from individual heartbeats of a patient, e.g., ST elevation, T wave amplitude, and QRS area measures. Local features may also include patient clinical information input into the device, such as the patient's age and sex. Global features, on the other hand, are comprised of projection coefficients that are calculated as earlier described.

Figure 5:
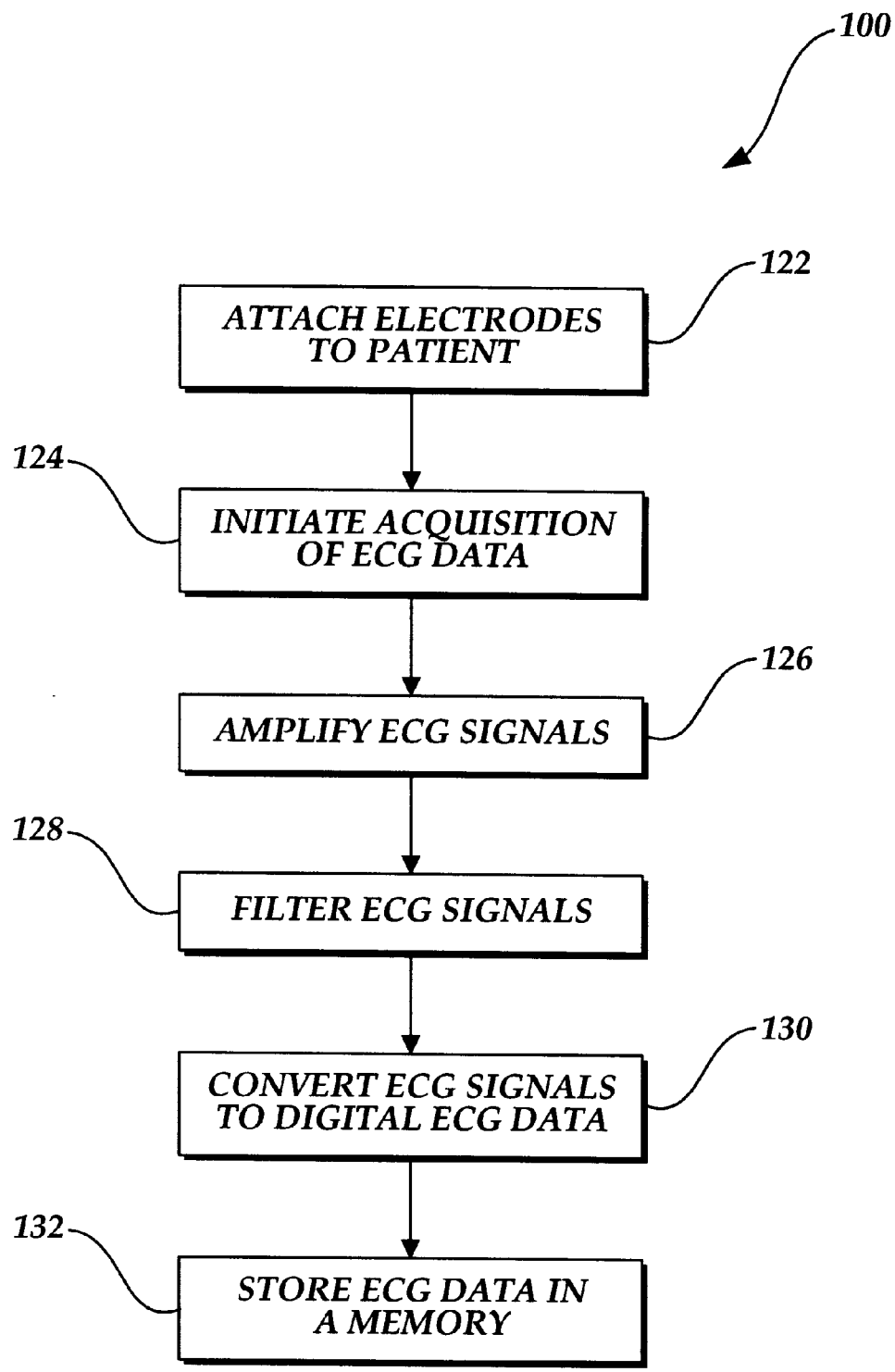
FIG. 5 is a flow diagram illustrating a process used to acquire ECG data for the acute cardiac ischemia detection process shown in FIG. 4.

In the manner earlier described in reference to FIGS. 4–6, in a block 170, the device 10 acquires about ten seconds of ECG data that is amplified and filtered. In a block 172, the device 10 then generates representative heartbeat data for each of the available leads. At that point, in either a parallel or sequential fashion, a set of global features are determined in blocks 176, 178, and 180, and a set of local features are determined in blocks 184 and 186 by the device 10.

To determine the set of global features, the device 10 categorizes a patient's ECG into a group (e.g., inferior, anterior, or other, as earlier described) and selects the applicable sets of basis vectors in block 176. The patient's representative heartbeat data is concatenated in block 178 into a concatenated heartbeat vector $\underline{x}$. Global features are calculated in block 180 by projecting the concatenated representative heartbeat vector $\underline{x}$ onto the selected basis vectors for the acute cardiac ischemic and non-ischemic ECG subspaces. The global features are then concatenated and input into a classifier in block 182 to compute a global classification statistic. As discussed earlier, a classifier suitable for use with this aspect of the present invention is a multidimensional Gaussian classifier that evaluates the global features relative to mean global features weighted by corresponding covariance matrices. At this time, however, the resulting global classification statistic is not compared with a decision threshold but instead is provided to a combiner in a block 190.

To determine the set of local features, one or more local morphological measures are calculated from the representative heartbeats in block 184. Patient clinical information, such as the age and sex of the patient, may also be obtained in block 186 from the user of the device 10. With regard to sex information, a "1" may be used for males and a "0" may be used for females. If clinical information is not entered or available at this time, default values may be used. While clinical information may improve accuracy in the detection of acute cardiac ischemia, the ECG classification of the present invention can be performed without this information. The values of the one or more local morphological measures and clinical information are concatenated to form a local feature vector that is input into a local feature classifier in a block 188 that computes a local classification statistic. The local classification statistic is not compared with a decision threshold at this time, but instead is also provided to the combiner in block 190.

The local feature classifier in block 188 may be either a statistical classifier or a heuristic classifier. A suitable statistical classifier for this aspect of the invention may be one similar in form to the Gaussian classifier used for classifying global features and described above. In that regard, the local feature classifier in block 188 is trained in a similar fashion using selected local morphological measures and clinical information as features derived from both ischemic and non-ischemic training populations. The selected local features for each training population, or group within a population, are concatenated to form local feature vectors from which a mean local feature vector is calculated. The corresponding local features of the patient are evaluated, using Equation (4), against the mean local feature vectors. The result of this evaluation is a local classification statistic that is provided to the combiner in block 190 as noted above.

Alternatively, a heuristic classifier may be used. A heuristic classifier tries to mimic procedures used by an expert (i.e., a cardiologist) to evaluate an ECG and report a diagnosis. A heuristic classifier compares the local features to expert-determined thresholds. For an expanded description of a suitable heuristic classifier, see G. Wagner, *Marriott's Practical Electrophysiology*, 9th Ed. (1994), published by Williams & Wilkins, Baltimore, which is incorporated herein by reference. The result of the evaluation is a local classification statistic that is supplied to the combiner in block 190.

As another alternative, or in addition to directly inputting a patient's local morphological measures and clinical information as local features into a local feature classifier, one or more composite local features derived from the local morphological measures and clinical information may be calculated and input into the local feature classifier. In one actual embodiment of the invention, two different procedures are used for calculating composite local features. One procedure involves using a logistic regression equation to produce a preliminary prediction of whether acute cardiac ischemia is present. The logistic regression equation is derived during a preprocessing training phase (e.g., the training phase described earlier in which the basis vectors and classifier parameters, i.e., the preprocessed parameters 67, are derived) according to a logistic regression model defined by the following equation.

$$\log\left(\frac{p}{1-p}\right) = a_0 + \sum_{i=1}^{K} a_i x_i \quad (5)$$

In Equation (5), "p" denotes the probability of detected acute cardiac ischemia, $a_o$ is a calculated constant, $a_i$ denotes the calculated $i^{th}$ regression coefficient, and $x_i$ denotes the $i^{th}$ explanatory variable (in this case, the local features of a patient). During the training phase, the probability of detected acute cardiac ischemia is known (i.e., the probability of ischemia is 1 for the ischemic training population and the probability of ischemia is 0 for the non-ischemic training population). Using the known probability information and the local features of the patients in the respective training populations, the regression coefficients of the logistic regression equation are determined in accordance with Equation (5). The regression coefficients are stored as preprocessed parameters 67 in the memory 64 (FIG. 3) for later use in producing a probability of detected acute cardiac ischemia in the patient under current evaluation.

If the training populations are divided into groups (e.g., anterior, inferior, and other) as described earlier, a logistic regression equation is derived for each of the groups. In that regard, ECG features and leads known to be associated with anterior acute cardiac ischemic events (e.g., the leads used in calculating the composite ST elevation measure $u_3$ discussed above) are selected for use in deriving the regression coefficients of an "anterior" logistic regression equation. Likewise, the ECG features and leads known to be associated with acute cardiac ischemia in an inferior or other location (e.g., the leads used in calculating the composite ST elevation measures $u_1$ or $u_2$ discussed above) are selected for use in deriving an "inferior" and an "other" logistic regression equation. The regression coefficients derived for each of the groups is stored as preprocessed parameters 67 in the memory 64 for later use in calculating a probability of detected acute cardiac ischemia in the patient under current evaluation.

For the patient under current evaluation, the patient's local features are input into the logistic regression equation derived during the training phase described above. More specifically, the patient's local features are weighted by the derived regression coefficients and combined as shown in Equation (5) to produce an output "p." The output "p" (i.e., the probability of detected acute cardiac ischemia) is used as a composite local feature to be classified in the local feature classifier in block 188. Where a logistic regression equation is derived for each of an anterior, inferior, and other group, a probability of detected acute cardiac ischemia in the current patient (i.e., a composite local feature) is calculated with respect to each of the groups. Thus, in that regard, an "anterior" composite local feature, and "inferior" composite local feature, and an "other" composite local feature are calculated for the current patient and input into the local feature classifier.

Alternatively, rather than directly inputting the composite local features into the local feature classifier in block 188, it may be advantageous to first dichotomize the composite local features. For instance, if the composite local feature sensitive to anterior acute cardiac ischemia exceeds a pre-selected threshold, the composite local feature is assigned a value of "1" (indicating predicted anterior acute cardiac ischemia). If the composite local feature does not exceed the threshold, it is assigned a value of "0" (indicating predicted non-ischemia). Similarly, dichotomized outputs "1" and "0" may be determined for the composite local features sensitive to inferior and other locations of acute cardiac ischemia. The thresholds used to dichotomize the composite local features are selected based on prediction patterns observed in the training populations during the training phase. The dichotomized composite local features are then input into the local feature classifier in block 188. For additional description of constructing and implementing logistic regression models, see D. Hosmer and S. Lemeshow, *Applied Logistic Regression* (1989), John Wiley & Sons, New York, incorporated by reference herein.

Another procedure for creating a composite local feature involves calculating a Mahalanobis distance. A Mahalanobis distance "d" is calculated according to Equation (4) and measures the distance between the patient's set of local features and a representative set of local features derived from a training population. A Mahalanobis distance $d_{isc}$ and/or $d_{non}$, calculated using representative local features from ischemic and/or non-ischemic training populations, may be provided as composite local features to the local feature classifier in block 188.

In implementations of the invention where ECGs are categorized into groups (e.g., anterior, inferior, and other), a Mahalanobis distance may be calculated for a patient's local features with respect to each of the anterior, inferior, and other groups. Using a nearest-neighbor approach, the patient's local features are then identified with a group (either anterior, inferior, other, or non-ischemia) according to the closest calculated distance. This group identification is provided as a composite local feature to the local feature classifier in block 188. Preferably, the local feature classifier in block 188 receives more than one composite local feature, including one or more dichotomized composite local features derived by logistic regression and one or more composite local features derived from calculating a Mahalanobis distance.

The local feature classifier in block 188 receiving the composite local features may use a logistic regression model such as that described above in reference to Equation (5) to determine acute cardiac ischemia from non-ischemia based on the composite local features. In a manner as described above, regression coefficients for a logistic regression equation are derived during the training phase by applying the composite local features derived from patients in the training populations with the known outcome of ischemia or non-ischemia in the populations. The regression coefficients are stored as preprocessed parameters 67 in the memory 64 (FIG. 3) for later use in determining the probability of acute cardiac ischemia in the patient under current evaluation. The probability of acute cardiac ischemia produced from the local feature classifier in block 188 is a local classification statistic that is supplied to the combiner in block 190 for evaluation in combination with the global classification statistic.

The combiner in block 190 is a classifier that receives the classification statistics from both the global and local feature classifiers (i.e., from blocks 182 and 188, respectively). The combiner is preferably a statistical classifier that uses a simple statistical model, such as a linear discriminate classifier or logistic discriminate classifier. The combiner evaluates the global and local classification statistics to produce a combined classification statistic that is compared against a threshold "t". If the combined classification statistic exceeds the threshold "t", the local and global classification statistics are classified as belonging to a class of patients experiencing acute cardiac ischemia. On the other hand, if the combined classification statistic is less than the threshold "t", the local and global classification statistics are classified as belonging to a non-ischemic class of patients. Suitable classifiers for use in the combiner in block 190 are discussed by R. Duda and P. Hart in *Pattern Classification and Scene Analysis*, referenced above. The result of the classification made by the combiner (i.e., whether or not acute cardiac ischemia is present) is then reported to the user in a block 192.

Figure 14:
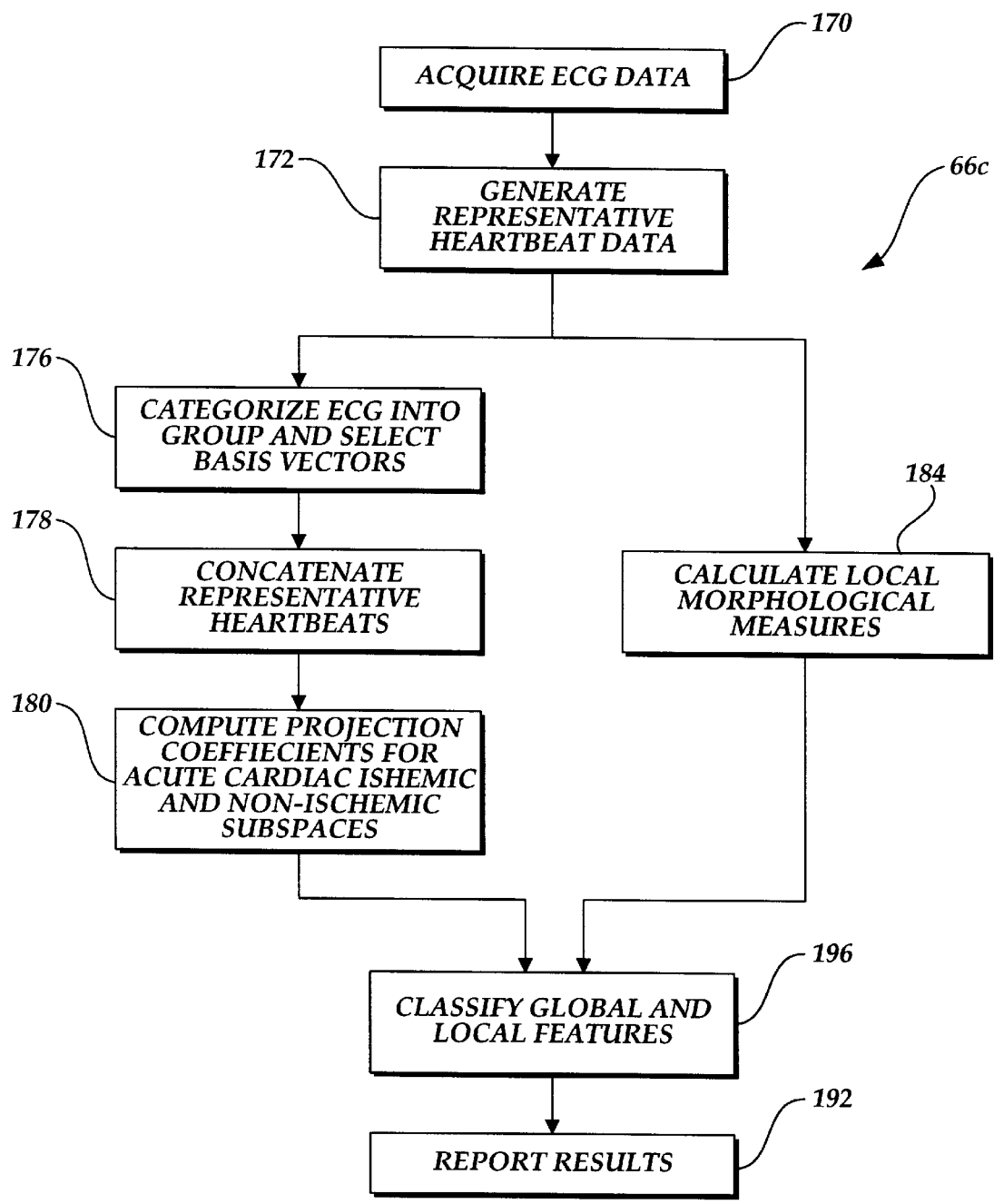
FIG. 14 is a flow diagram illustrating an alternative acute cardiac ischemia detection process conducted by the device shown in FIGS. 2 and 3 which detects acute cardiac ischemic events by classifying a combination of global and local features.

FIG. 14 is a flow diagram that illustrates another alternative version of an acute cardiac ischemia detection process 66c formed in accordance with the present invention in which both global and local features are evaluated. In FIG. 14, a single classifier is used in a block 196 in place of the separate global and local classifiers (blocks 182 and 188, respectively) and the combiner (block 190) described in reference to FIG. 13. The single classifier in block 196 receives both the global features computed in block 180 and the local features calculated in block 184 as features to be jointly classified. Patient clinical information may also be input into the classifier in block 196 as additional local features (though not shown in FIG. 14). Alternatively, or in addition to the local features discussed above, composite local features may be calculated and provided to the classifier in block 196 along with the global features.

The classifier in block 196 may be a statistical classifier having a form similar to the classifiers described above. For example, the classifier may be a Gaussian classifier previously trained during a preprocessing training phase using corresponding sets of global and local features derived from patients in the ischemic and non-ischemic training populations. The current patient's global features and local features are concatenated into a single global/local feature vector. The classifier then evaluates the patient's combined global/local feature vector with respect to calculated representative global/local feature vectors derived from the ischemic and non-ischemic populations to produce a classification global/local statistic. The global/local classification statistic is then compared with a selected threshold to produce a diagnosis of whether an acute cardiac ischemic condition is present. In an actual embodiment of the present invention, a logistic regression classifier is used to evaluate the combined global/local feature set. For additional detail on a logistic regression classifier, see D. Hosmer and S. Lemeshow, *Applied Logistic Regression* (1989), referenced above. Depending on the outcome of the evaluation performed by the classifier in block 196, a report indicating detection of acute cardiac ischemia is produced in block 192.

It should be understood that a classifier is typically implemented as a computer software routine. In reference to FIG. 3, a classifier executed by the processing unit 62 forms part of a computer program that carries out the functions of the acute cardiac ischemia detection process 66. Alternatively, a classifier executed by the processing unit 62 may comprise a separate software routine implemented by a separate processor or circuit in communication with the processing unit 62.

Figure 15:
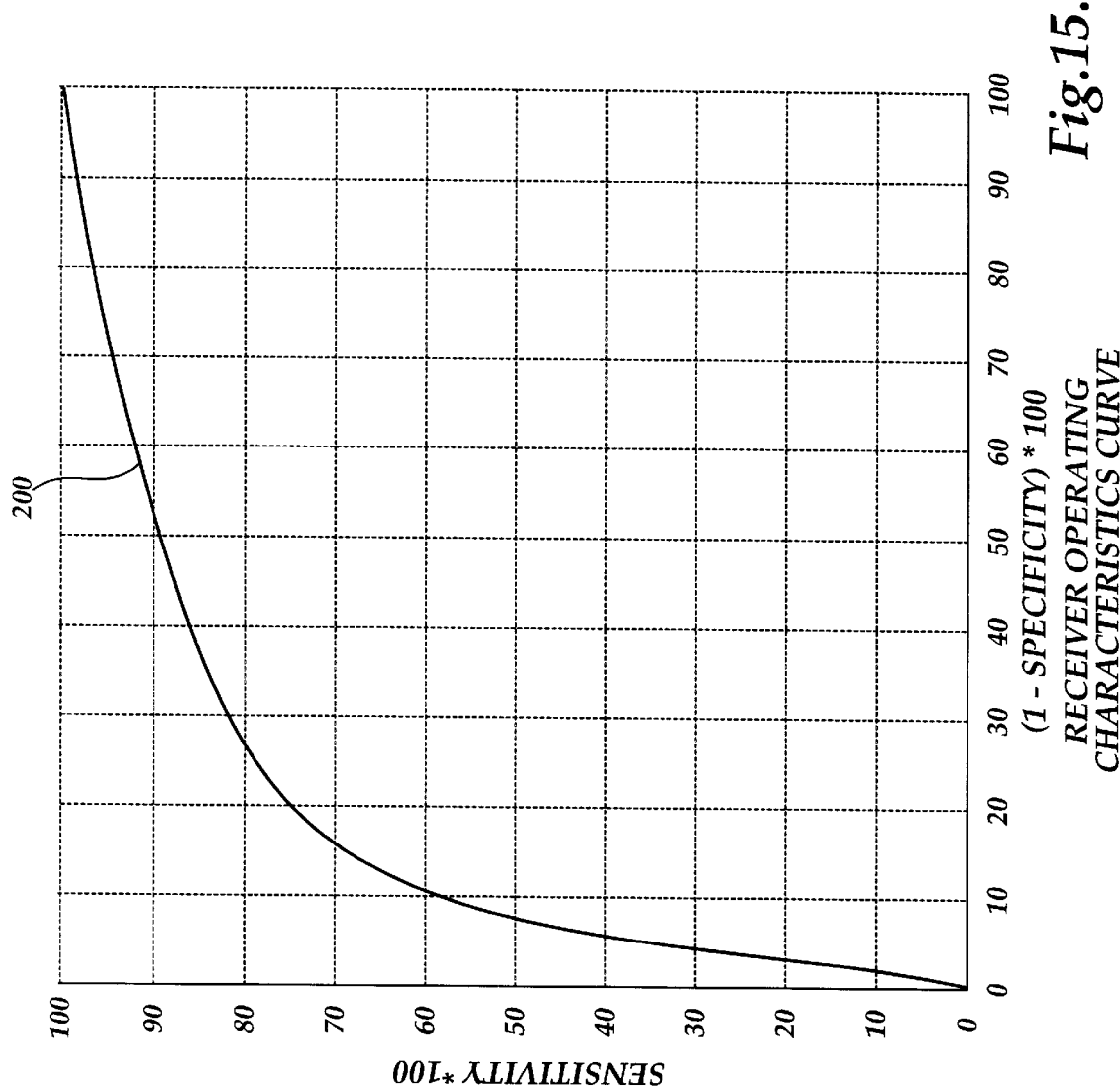
FIG. 15 is a graph of a typical receiver operating characteristics curve depicting sensitivity/specificity tradeoffs which can be implemented by the device shown in FIGS. 2 and 3.

The ability to identify and correctly diagnose acute cardiac ischemic events is indicated by the sensitivity and specificity of the device 10. As noted earlier, a typical sensitivity/specificity tradeoff is illustrated by a receiver operating characteristics (ROC) curve 200 as shown in FIG. 15. The y-axis in FIG. 15 represents sensitivity, or fraction of true positives detected, and the x-axis represents the quantity of "1-specificity", or fraction of false positives detected. Values on both axes are expressed as percentages. Thus, as shown in FIG. 15, a detection device 10 tuned to be more sensitive in its analysis is typically less specific, and a device tuned to be more specific is typically less sensitive. If the device 10 could correctly diagnose all cases, the analysis would have a specificity of one and a sensitivity of one. In the present invention, the point at which a detection device 10 operates on its ROC curve may be adjusted by varying the decision threshold "t" against which the calculated classification statistic (described earlier) is compared.

In one embodiment of the invention, the decision threshold, and hence the sensitivity/specificity operating point of the detection device 10, is set at the time of manufacture in the software that carries out the acute cardiac ischemia detection process 66. Alternatively, the threshold may be adjusted at the point of sale of the device according to the purchaser's needs by adjusting appropriate variables in the software or by setting an internal dial or switch that is read by the software. The device 10 may further be configured to receive a user input (e.g., an external dial, switch, or key input) that selectively adjusts the threshold used by the software, and thus adjusts the sensitivity/specificity operating point of the device.

Figure 16:
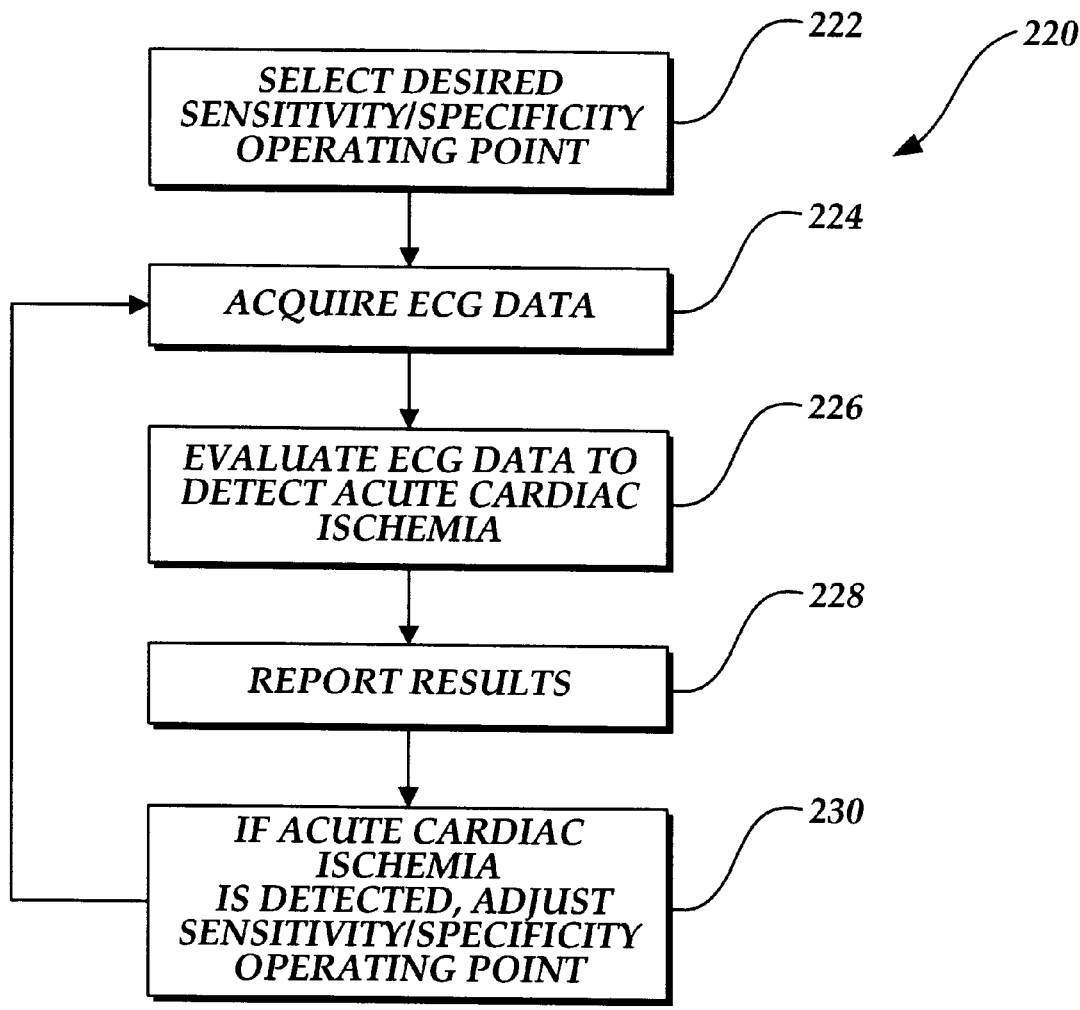
FIG. 16 is a flow diagram illustrating an acute cardiac ischemia detection process conducted by the device shown in FIGS. 2 and 3 wherein the sensitivity/specificity operating point of the device is adjusted to achieve a desired sensitivity/specificity tradeoff as shown in FIG. 15.

A device 10 constructed with an adjustable sensitivity/specificity tradeoff according to the present invention may be used for screening patients with possible acute cardiac ischemia as well as confirming a detected ischemic condition for treatment purposes. FIG. 16 is a flow diagram illustrating an acute cardiac ischemia detection process 220 for screening and confirming a detected acute cardiac ischemic condition. In a block 222, a desired sensitivity/specificity operating point for the device is selected either by the manufacturer, purchaser, or user. In that regard, to screen patients for possible acute cardiac ischemia, it is generally preferred that the sensitivity/specificity operating point of the device be set for a high level of sensitivity.

In a block 224, the device 10 acquires ECG data and, in a block 226, the device evaluates the ECG data to detect acute cardiac ischemia as described by the acute cardiac ischemia detection processes 66a, 66b, or 66c shown in FIGS. 4, 13, or 14. In a block 228, the device 10 reports the results of the acute cardiac ischemia detection process via a user display. In a block 230, if acute cardiac ischemia is detected, the user of the device is given opportunity to adjust the sensitivity/specificity operating point to a higher level of specificity for a second evaluation of the patient.

After adjusting the sensitivity/specificity operating point in block 230, the device 10 performs a second evaluation of the patient by returning to block 224 to acquire ECG data from the patient. The patient's ECG data is analyzed and evaluated in block 226 using the adjusted sensitivity/specificity operating point to confirm whether an acute cardiac ischemic condition has been detected. The result of the second evaluation is reported in block 228. It is appreciated that additional evaluations of the patient may be performed as desired.

Although FIG. 16 illustrates a second evaluation being performed on newly acquired ECG data (i.e., by returning to block 224 from block 230), it should be understood that a second and additional evaluations may be performed on the original set of ECG data acquired from the patient in the first evaluation. In that regard, rather than returning to block 224 from block 230, the device 10 would return to block 226 to reevaluate the original ECG data using the adjusted sensitivity/specificity operating point.

While various embodiments of the invention have been illustrated and described herein, it is appreciated that changes may be made without departing from the spirit and scope of the invention. For example, rather than concatenating the representative heartbeat data on each of the leads and projecting the concatenated heartbeat vector onto the basis vectors, each of the particular leads may be individually projected onto a set of basis vectors derived for the particular lead and the resulting projection coefficients may be used as global features. It should also be understood that with sufficient human expert evaluation of global features, classifying the set of global features may be performed heuristically. Furthermore, when reporting whether an acute cardiac ischemic condition is detected, a device constructed according to the invention may report an outcome in a range of outcomes (e.g., the likelihood of acute cardiac ischemia on a scale of 1–10) instead of reporting a binary "yes/no" result. In that regard, rather than comparing a calculated classification statistic to a single threshold (to produce a binary result), the classification statistic may be quantized into a range of values and the closest value in the range of values is reported to the user. It is intended, therefore, that the scope of the invention be determined from the claims that follow and equivalents thereto.

The embodiments of the invention in which an exclusive property or privilege is claimed are defined as follows:

1. A method of detecting and reporting a condition associated with acute cardiac ischemia in a patient, comprising:
   (a) obtaining one or more leads of ECG data from the patient;
   (b) deriving heartbeat data from the patient's ECG data;
   (c) forming a vector of heartbeat data from the derived heartbeat data;
   (d) producing a set of global features by projecting the vector of heartbeat data onto one or more basis vectors that define an acute cardiac ischemic ECG subspace or a non-ischemic ECG subspace;
   (e) classifying the set of global features to determine whether the global features are indicative of an acute cardiac ischemic condition; and
   (f) reporting whether the acute cardiac ischemic condition is determined to be present.

2. The method of claim 1, wherein forming the vector of heartbeat data includes:
   (a) analyzing the one or more leads of ECG data to identify one or more heartbeats;
   (b) generating representative heartbeat data for each lead; and
   (c) concatenating the representative heartbeat data for each lead to form the vector of heartbeat data.

3. The method of claim 1, wherein producing the set of global features includes:
   (a) calculating an inner product of the vector of heartbeat data and one or more basis vectors that define the acute cardiac ischemic ECG subspace to produce a corresponding number of ischemic condition projection coefficients;
   (b) calculating an inner product of the vector of heartbeat data and one or more basis vectors that define the non-ischemic ECG subspace to produce a corresponding number of non-ischemic condition projection coefficients; and
   (c) using the ischemic condition projection coefficients and the non-ischemic condition projection coefficients as the set of global features.

4. The method of claim 1, further comprising:
   (a) defining a plurality of groups wherein each group has basis vectors associated therewith that define a group-specific acute cardiac ischemic ECG subspace and a group-specific non-ischemic ECG subspace;
   (b) categorizing the patient's ECG data into a group in the plurality of groups; and
   (c) using the basis vectors of the group into which the patient's ECG data is categorized as the basis vectors onto which the vector of heartbeat data is projected.

5. The method of claim 4, wherein categorizing the patient's ECG data into a group includes:
   (a) selecting a local feature derived from the patient; and
   (b) categorizing the patient's ECG data into a group based on the selected local feature.

6. The method of claim 4, further comprising:
   (a) defining each group of the plurality of groups to correspond to a location of an acute cardiac ischemic condition; and
   (b) if the acute cardiac ischemic condition is determined to be present, reporting the location of the acute cardiac ischemic condition corresponding to the group into which the patient's ECG data is categorized.

7. The method of claim 4, wherein categorizing the patient's ECG data into a group includes:
   (a) calculating the ST elevation of one or more of the leads obtained from the patient;
   (b) forming subgroups of the leads for which ST elevation was calculated;
   (c) calculating a composite ST elevation for each subgroup by calculating a mathematical combination of the ST elevation of the leads in each subgroup; and
   (d) categorizing the patient's ECG into a group according to the subgroup whose composite ST elevation is greatest.

8. The method of claim 4, further comprising:
   (a) measuring an ST elevation on the one or more leads of ECG data obtained from the patient; and
   (b) categorizing the patient's ECG data into a group based on the measured ST elevation.

9. The method of claim 1, further comprising:
   (a) using a Karhunen-Loeve transformation to calculate a first set of basis vectors that define the acute cardiac ischemic ECG subspace and a second set of basis vectors that define the non-ischemic ECG subspace;
   (b) selecting one or more basis vectors from the first set of basis vectors and one or more basis vectors from the second set of basis vectors as the basis vectors onto which the vector of heartbeat data is projected.

10. The method of claim 1, wherein classifying the set of global features includes:
    (a) concatenating the set of global features to form a global feature vector;
    (b) producing a classification statistic by evaluating the global feature vector relative to a representative global feature vector derived from a training population; and
    (c) comparing the classification statistic with a threshold to determine whether the global features are indicative of the acute cardiac ischemic condition.

11. The method of claim 6, wherein a Gaussian classifier is used to evaluate the global feature vector relative to the representative global feature vector and produce the classification statistic.

12. The method of claim 10, further comprising selecting the threshold in accordance with a desired sensitivity/specificity tradeoff.

13. The method of claim 1, wherein if the one or more basic vectors define only the acute cardiac ischemic ECG subspace, or if the one or more basis vectors define only the non-ischemic ECG subspace, then classifying the set of global features includes:
  (a) concatenating the set of global features to form a global feature vector;
  (b) producing a classification statistic based on a calculated distance between the global feature vector and a representative global feature vector derived from a training population; and
  (c) comparing the classification statistic with a threshold to determine whether the global features are indicative of the acute cardiac ischemic condition.

14. A device for detecting and reporting a condition associated with acute cardiac ischemia in a patient, comprising:
  (a) a plurality of electrodes for sensing patient ECG signals;
  (b) a processing unit in communication with the plurality of electrodes the processing unit configured to:
    (i) derive heartbeat data from the patient's ECG data;
    (ii) form a vector of heartbeat data from the derived heartbeat data;
    (iii) produce a set of global features by projecting the vector of heartbeat data onto one or more predetermined basis vectors that define an acute cardiac ischemic ECG subspace or a non-ischemic ECG subspace; and
    (iv) classify the set of global features to determine whether the global features are indicative of an acute cardiac ischemic condition; and
  (c) a user output in communication with the processing unit for reporting whether the acute cardiac ischemic condition is determined to be present.

15. The device of claim 14, wherein the processing unit is configured to classify the set of global features to produce a first output, and wherein the processing unit is further configured to:
  (a) obtain a set of local features from the patient;
  (b) classify the set of local features obtained from the patient to produce a second output; and
  (c) classify the first and second outputs to determine whether the first and second outputs are indicative of the acute cardiac ischemic condition.

16. The device of claim 14, wherein the processing unit is configured to obtain a set of local features from the patient and classify the set of local features in combination with the set of global features to determine whether the acute cardiac ischemic condition is present.

17. A method of detecting and reporting a condition associated with acute cardiac ischemia in a patient, comprising:
  (a) obtaining one or more leads of ECG data from the patient;
  (b) deriving heartbeat data from the patient's ECG data;
  (c) forming a vector of heartbeat data from the derived heartbeat data;
  (d) generating a local classification statistic by:
    (i) deriving a set of local features from the patient; and
    (ii) classifying the set of local features to produce the local classification statistic;
  (e) generating a global classification statistic by:
    (i) producing a set of global features by projecting the vector of heartbeat data onto one or more basis vectors that define an acute cardiac ischemic ECG subspace or a non-ischemic ECG subspace; and
    (ii) classifying the set of global features to produce the global classification statistic;
  (f) classifying the local classification statistic and the global classification statistic to determine whether the local and global classification statistics are indicative of an acute cardiac ischemic condition; and
  (g) reporting whether the acute cardiac ischemic condition is determined to be present.

18. The method of claim 17, wherein forming the vector of heartbeat data includes:
  (a) analyzing the one or more leads of ECG data to identify one or more heartbeats;
  (b) generating representative heartbeat data for each lead; and
  (c) concatenating the representative heartbeat data for each lead to form the vector of heartbeat data.

19. The method of claim 17, wherein classifying the set of local features includes:
  (a) concatenating the set of local features to form a local feature vector; and
  (b) evaluating the local feature vector relative to a representative local feature vector derived from a training population to produce the local classification statistic.

20. The method of claim 17, wherein classifying the set of local features includes:
  (a) applying one or more local features in the set of local features to a logistic regression equation to produce a probability of detection that is used as a composite local feature;
  (b) dichotomizing the composite local feature; and
  (c) classifying the dichotomized composite local feature in producing the local classification statistic.

21. The method of claim 17, wherein classifying the set of local features includes:
  (a) concatenating the set of local features to form a local feature vector;
  (b) calculating a Mahalanobis distance between the local feature vector and a representative local feature vector derived from a training population, wherein the Mahalanobis distance is used as a composite local feature; and
  (c) classifying the composite local feature in producing the local classification statistic.

22. The method of claim 21, further comprising:
  (a) dividing the training population into a plurality of groups;
  (b) deriving a representative local feature vector for each group;
  (c) calculating a Mahalanobis distance between the local feature vector and the representative local feature vector for each group in the plurality of groups, resulting in a plurality of composite local features; and
  (d) classifying the plurality of composite local features in producing the local classification statistic.

23. The method of claim 17, wherein classifying the set of local features includes:
  (a) defining a plurality of groups, wherein each group has a representative local feature vector associated therewith that is derived from a training population;
  (b) concatenating the set of local features to form a local feature vector;
  (c) for each group, calculating a Mahalanobis distance between the local feature vector and the representative local feature vector associated with the group;

(d) identifying the local feature vector with one of the groups based on the Mahalanobis distance calculated for each group, the group identification being used as a composite local feature; and (e) classifying the composite local feature in producing the local classification statistic.

24. The method of claim 17, wherein classifying the set of local features includes:

(a) defining a plurality of groups wherein each group has a logistic regression equation associated therewith, the logistic regression equation for each group having regression coefficients derived from a logistic regression model using selected local features of a training population;

(b) applying corresponding selected local features derived from the patient to the logistic regression equation associated with each group to produce for each group a probability of detection that is used as a composite local feature; and (c) classifying the composite local features in producing the local classification statistic.

25. The method of claim 17, wherein producing the set of global features includes:

(a) calculating an inner product of the vector of heartbeat data and one or more basis vectors that define the acute cardiac ischemic ECG subspace to produce a corresponding number of ischemic condition projection coefficients;

(b) calculating an inner product of the vector of heartbeat data and one or more basis vectors that define the non-ischemic ECG subspace to produce a corresponding number of non-ischemic condition projection coefficients; and (c) using the ischemic condition projection coefficients and the non-ischemic condition projection coefficients as the set of global features.

26. The method of claim 17, further comprising:

(a) defining a plurality of groups wherein each group has basis vectors associated therewith that define a group-specific acute cardiac ischemic ECG subspace and a group-specific non-ischemic ECG subspace;

(b) categorizing the patient's ECG data into a group in the plurality of groups; and (c) using the basis vectors of the group into which the patient's ECG data is categorized as the basis vectors onto which the vector of heartbeat data is projected.

27. The method of claim 26, wherein categorizing the patient's ECG data into a group includes:

(a) selecting a local feature derived from the patient; and (b) categorizing the patient's ECG data into a group based on the selected local feature.

28. The method of claim 26, further comprising:

(a) measuring an ST elevation on the one or more leads of ECG data obtained from the patient; and (b) categorizing the patient's ECG data into a group based on the measured ST elevation.

29. The method of claim 26, further comprising:

(a) defining each group of the plurality of groups to correspond to a location of the acute cardiac ischemic condition; and (b) if the acute cardiac ischemic condition is determined to be present, reporting the location of the acute cardiac ischemic condition corresponding to the group into which the patient's ECG data is categorized.

30. The method of claim 26, wherein categorizing the patient's ECG data into a group includes:

(a) calculating the ST elevation of one or more of the leads obtained from the patient;

(b) forming subgroups of the leads for which ST elevation was calculated;

(c) calculating a composite ST elevation for each subgroup by calculating a mathematical combination of the ST elevation of the leads in each subgroup; and (d) categorizing the patient's ECG into a group according to the subgroup whose composite ST elevation is greatest.

31. The method of claim 17, further comprising:

(a) using a Karhunen-Loeve transformation to calculate a first set of basis vectors that define the acute cardiac ischemic ECG subspace and a second set of basis vectors that define the non-ischemic ECG subspace;

(b) selecting one or more basis vectors from the first set of basis vectors and one or more basis vectors from the second set of basis vectors as the basis vectors onto which the vector of heartbeat data is projected.

32. The method of claim 17, wherein classifying the set of global features includes:

(a) concatenating the set of global features to form a global feature vector; and (b) evaluating the global feature vector relative to a representative global feature vector derived from a training population to produce the global classification statistic.

33. The method of claim 32, wherein a Gaussian classifier is used to evaluate the global feature vector relative to the representative global feature vector and produce the global classification statistic.

34. The method of claim 17, wherein classifying the local and global classification statistics includes:

(a) producing a combined classification statistic by evaluating the local and global classification statistics relative to corresponding representative local and global classification statistics derived from a training population; and (b) comparing the combined classification statistic with a threshold to determine whether the local and global classification statistics are indicative of the acute cardiac ischemic condition.

35. The method of claim 34, further comprising selecting the threshold in accordance with a desired sensitivity/specificity tradeoff.

36. A method of detecting and reporting a condition associated with acute cardiac ischemia in a patient, comprising:

(a) obtaining one or more leads of ECG data from the patient;

(b) deriving heartbeat data from the patient's ECG data;

(c) forming a vector of heartbeat data from the derived heartbeat data;

(d) deriving a set of local features from the patient;

(e) producing a set of global features by projecting the vector of heartbeat data onto one or more basis vectors that define an acute cardiac ischemic ECG subspace or a non-ischemic ECG subspace;

(f) jointly classifying the set of global features and the set of local features to determine whether the global features and local features are indicative of an acute cardiac ischemic condition; and (g) reporting whether the acute cardiac ischemic condition is determined to be present.

37. The method of claim 36, wherein forming the vector of heartbeat data includes:
(a) analyzing the one or more leads of ECG data to identify one or more heartbeats;
(b) generating representative heartbeat data for each lead; and
(c) concatenating the representative heartbeat data for each lead to form the vector of heartbeat data.

38. The method of claim 36, wherein the set of local features jointly classified with the set of global features includes a dichotomized composite local feature calculated by:
(a) applying one or more local features derived from the patient to a logistic regression equation to produce a probability of detection that is used as a composite local feature; and
(b) dichotomizing the composite local feature.

39. The method of claim 36, wherein the set of local features jointly classified with the set of global features includes a composite local feature calculated by concatenating the set of local features to form a local feature vector and calculating a Mahalanobis distance between the local feature vector and a representative local feature vector derived from a training population, the Mahalanobis distance being used as the composite local feature.

40. The method of claim 39, further comprising:
(a) dividing the training population into a plurality of groups;
(b) deriving a representative local feature vector for each group;
(c) calculating a Mahalanobis distance between the local feature vector and the representative local feature vector for each group, resulting in a plurality of composite local features; and
(d) including the plurality of composite local features in the set of local features jointly classified with the set of global features.

41. The method of claim 36, further comprising:
(a) concatenating the set of local features to form a local feature vector;
(b) defining a plurality of groups, and for each group, deriving a representative local feature vector from a training population;
(c) calculating a Mahalanobis distance for each group measured between the local feature vector and the representative local feature vector associated with each group;
(d) identifying the local feature vector with one of the groups based on the Mahalanobis distance calculated for each group, the group identification being used as a composite local feature; and
(e) jointly classifying the composite local feature with the set of global features and the set of local features to determine the presence of the acute cardiac ischemic condition in the patient.

42. The method of claim 36, wherein the set of local features jointly classified with the set of global features includes composite local features calculated by:
(a) defining a plurality of groups wherein each group has a logistic regression equation associated therewith, the logistic regression equation for each group having regression coefficients derived from a logistic regression model using selected local features of a training population; and
(b) applying corresponding selected local features derived from the patient to the logistic regression equation associated with each group to produce for each group a probability of detection that is used as a composite local feature.

43. The method of claim 36, wherein producing the set of global features includes:
(a) calculating an inner product of the vector of heartbeat data and one or more basis vectors that define the acute cardiac ischemic ECG subspace to produce a corresponding number of ischemic condition projection coefficients;
(b) calculating an inner product of the vector of heartbeat data and one or more basis vectors that define the non-ischemic ECG subspace to produce a corresponding number of non-ischemic condition projection coefficients; and
(c) using the ischemic condition projection coefficients and the non-ischemic condition projection coefficients as the set of global features.

44. The method of claim 36, further comprising:
(a) defining a plurality of groups wherein each group has basis vectors associated therewith that define a group-specific acute cardiac ischemic ECG subspace and a group-specific non-ischemic ECG subspace;
(b) categorizing the patient's ECG data into a group in the plurality of groups; and
(c) using the basis vectors of the group into which the patient's ECG data is categorized as the basis vectors onto which the vector of heartbeat data is projected.

45. The method of claim 44, wherein categorizing the patient's ECG data into a group includes:
(a) selecting a local feature derived from the patient; and
(b) categorizing the patient's ECG data into a group based on the selected local feature.

46. The method of claim 44, further comprising:
(a) defining each group of the plurality of groups to correspond to a location of the acute cardiac ischemic condition; and
(b) if the acute cardiac ischemic condition is determined to be present, reporting the location of the acute cardiac ischemic condition corresponding to the group into which the patient's ECG data is categorized.

47. The method of claim 44, wherein categorizing the patient's ECG data into a group includes:
(a) calculating the ST elevation of one or more of the leads obtained from the patient;
(b) forming subgroups of the leads for which ST elevation was calculated;
(c) calculating a composite ST elevation for each subgroup by calculating a mathematical combination of the ST elevation of the leads in each subgroup; and
(d) categorizing the patient's ECG into a group according to the subgroup whose composite ST elevation is greatest.

48. The method of claim 44, further comprising:
(a) measuring an ST elevation on the one or more leads of ECG data obtained from the patient; and
(b) categorizing the patient's ECG data into a group based on the measured ST elevation.

49. The method of claim 36, further comprising:
(a) using a Karhunen-Loeve transformation to calculate a first set of basis vectors that define the acute cardiac ischemic ECG subspace and a second set of basis vectors that define the non-ischemic ECG subspace;

(b) selecting one or more basis vectors from the first set of basis vectors and one or more basis vectors from the second set of basis vectors as the basis vectors onto which the vector of heartbeat data is projected.

50. The method of claim 36, wherein jointly classifying the set of global features and the set of local features includes:

(a) concatenating the set of local features and the set of global features to form a global/local feature vector; and (b) producing a global/local classification statistic by evaluating the global/local feature vector relative to a representative global/local feature vector derived from a training population; and (c) comparing the global/local classification statistic with a threshold to determine whether the global features and local features are indicative of the acute cardiac ischemic condition.

51. The method of claim 50, wherein a Gaussian classifier is used to evaluate the global/local feature vector relative to the representative global/local feature vector and produce the global/local classification statistic.

52. The method of claim 50, further comprising selecting the threshold in accordance with a desired sensitivity/specificity tradeoff.

53. A device for detecting and reporting a condition associated with acute cardiac ischemia in a patient, comprising:

(a) electrodes adapted to be placed on the patient to sense ECG signals;

(b) a user input;

(b) a processing unit in communication with the user input and the electrodes, wherein the processing unit is configured to acquire ECG data from the ECG signals and determine the presence of an acute cardiac ischemic condition by:

(i) analyzing the ECG data;

(ii) calculating a classification statistic reflective of a cardiac condition based on at least one characteristic obtained from the ECG data; and (iii) comparing the classification statistic with a threshold that reflects a desired sensitivity/specificity operating point for the device, wherein the sensitivity/specificity operating point of the device is adapted to be selected by a user of the device via the user input; wherein the threshold used by the processing unit is automatically adjusted for higher specificity after the processing unit determines the presence of the acute cardiac ischemic condition in the patient.

54. A device for detecting and reporting a condition associated with acute cardiac ischemia in a patient, comprising:

(a) electrodes adapted to be placed on the patient to sense ECG signals;

(b) a processing unit in communication with the electrodes, wherein the processing unit is configured to acquire ECG data from the ECG signals and determine the presence of an acute cardiac ischemic condition by:

(i) forming a vector of heartbeat data from the ECG data;

(ii) projecting the vector of heartbeat data onto one or more predetermined basis vectors defining an acute cardiac ischemic ECG subspace or a non-ischemic ECG subspace to produce one or more global features;

(iii) calculating a classification statistic reflective of a cardiac condition based on the one or more global features; and (iv) comparing the classification statistic with a threshold that reflects a desired sensitivity/specificity operating point for the device.

55. The device of claim 54, wherein the device further includes a user input in communication with the processing unit and wherein the sensitivity/specificity operating point of the device is adapted to be selected by a user of the device via the user input.

* * * * *

UNITED STATES PATENT AND TRADEMARK OFFICE
CERTIFICATE OF CORRECTION

PATENT NO. : 6,171,256 B1
DATED : January 9, 2001
INVENTOR(S) : T.H. Joo et al.

It is certified that error appears in the above-identified patent and that said Letters Patent is hereby corrected as shown below:

Column 1, Item [56],
References Cited, (U.S. Patents), please insert in appropriate numerical order the following:

| | | | |
|---|---|---|---|
| -- | 5,520,191 | 5/1996 | Karlsson et al. |
| | 5,456,261 | 10/1995 | Luczyk |
| | 5,419,337 | 5/1995 | Dempsey et al. |
| | 5,410,473 | 4/1995 | Kaneko et al. |
| | 5,365,426 | 11/1994 | Siegel et al. |
| | 5,161,539 | 11/1992 | Evans et al. |
| | 5,159,932 | 11/1992 | Zanetti et al. |
| | 5,010,888 | 4/1991 | Jadvar et al. |
| | 4,924,875 | 5/1990 | Chamoun |
| | 4,974,598 | 12/1990 | John |
| | 4,802,491 | 2/1989 | Cohen et al. -- |

References Cited, (U.S. Patents), please insert in appropriate numerical order the following:
-- 4,121,576    10/1978    Greensite    --

References Cited, (U.S. Patents), please insert in appropriate numerical order the following:
-- 4,850,370    7/1989    Dower    --

Column 2, Item [56],
References Cited, (Foreign Patents), please insert in appropriate numerical order the following:
-- 0 467 695 A2    1/1992    (EP)    --

References Cited, (Foreign Patents), please insert in appropriate numerical order the following:
-- 1 281 174    7/1972    (GB)    --

Column 2, Item [74],
Attorney, Agent, or Firm, "O'Connor;" should read -- O'Connor --

Column 24,
Line 59, (Claim 11, line 1), "claim 6," should read -- claim 10, --

UNITED STATES PATENT AND TRADEMARK OFFICE
CERTIFICATE OF CORRECTION

PATENT NO. : 6,171,256 B1
DATED : January 9, 2001
INVENTOR(S) : T.H. Joo et al.

It is certified that error appears in the above-identified patent and that said Letters Patent is hereby corrected as shown below:

<u>Column 25,</u>
Line 20, (Claim 14, line 7), "electrodes" should read -- eletrodes, --

Signed and Sealed this

Sixth Day of November, 2001

*Attest:*

NICHOLAS P. GODICI
*Attesting Officer*     *Acting Director of the United States Patent and Trademark Office*